(12) United States Patent
Chen et al.

(10) Patent No.: US 8,309,582 B2
(45) Date of Patent: Nov. 13, 2012

(54) SMALL MOLECULE BCL-XL/BCL-2 BINDING INHIBITORS

(75) Inventors: Ching-Shih Chen, Upper Arlington, OH (US); Chung-Wai Shiau, San Diego, CA (US)

(73) Assignee: The Ohio State University Research Foundation, Columbus, OH (US)

( * ) Notice: Subject to any disclaimer, the term of this patent is extended or adjusted under 35 U.S.C. 154(b) by 285 days.

(21) Appl. No.: 12/652,456

(22) Filed: Jan. 5, 2010

(65) Prior Publication Data
US 2010/0168184 A1 Jul. 1, 2010

Related U.S. Application Data

(62) Division of application No. 11/315,077, filed on Dec. 22, 2005, now Pat. No. 7,714,005.

(60) Provisional application No. 60/638,519, filed on Dec. 22, 2004.

(51) Int. Cl.
- *A01N 43/40* (2006.01)
- *A01N 43/78* (2006.01)
- *A01N 43/80* (2006.01)
- *A61K 31/44* (2006.01)
- *A61K 31/425* (2006.01)
- *C07D 277/00* (2006.01)

(52) U.S. Cl. ........ 514/342; 514/365; 514/366; 514/373; 548/188

(58) Field of Classification Search .......... 514/342, 514/365, 366, 373; 548/188
See application file for complete search history.

(56) References Cited

U.S. PATENT DOCUMENTS

| | | | |
|---|---|---|---|
| 5,387,596 | A | 2/1995 | Takebayashi et al. |
| 5,801,173 | A | 9/1998 | Lohray et al. |
| 7,566,787 | B2 | 7/2009 | Chen |

FOREIGN PATENT DOCUMENTS

EP 0454501 A2 1/1991

OTHER PUBLICATIONS

Metabolomics [online], Retrieved from the Internet Apr. 24, 2008, www.en.wikipedia.org/wiki/Metabolomics.
Kwon, Younggil, Handbook of Essential Pharmacokinetics, Pharmacodynamics and Drug Metabolism for Industrial Scientists, Jun. 24, 2001.
Palakurthia, Sangeetha S., "Anticancer Effects of Thiazolidinediones are Independent of Peroxisome Proliferator-activated Receptory and Mediated by Inhibition of Translation Initiation", Cancer Reserch 61, 6213-6218, Aug. 15, 2001.
Qin, Chunhua, et al., "Peroxisome Proliferator-activated Receptory Agonists Induce Proteasome-dependent Degradation of Cyclin D1 and Estrogen Receptor a in MCF-7 Breast Cancer Cells", Cancer Research 63, 958-964, Mar. 1, 2003.
Cancer Topics [online], Retrieved from the Internet Apr. 24, 2008, www.nci/gov/cancertopics/druginfo/alphalist/print?page=&keyword, Alphabetical List of Drugs.
Office Action dated Jan. 11, 2008 from U.S. Appl. No. 11/315,569.
Response to Office Action dated Jan. 11, 2008 from U.S. Appl. No. 11/315,569, submitted Apr. 11, 2008.
Office Action dated May 19, 2008 from U.S. Appl. No. 11/315,569.
Response to Office Action dated May 19, 2008 from U.S. Appl. No. 11/315,569, submitted Nov. 19, 2008.
Notice of Allowance dated Mar. 24, 2009 from U.S. Appl. No. 11/315,569.
Amendment After Notice of Allowance from U.S. Appl. No. 11/315,569 submitted Apr. 21, 2009.
Golub et al., Science, vol. 286, Oct. 15, 1999, pp. 531-537.
International Search Report from PCT/US05/46454, May 16, 2006.
Gupta, Rajnish A, et al., "Target Genes of Peroxisome Proliferator-activated Receptor y in Colorectal Cancer Cells", J. Biol. Chem., vol. 275, No. 32, Aug. 10, 2001, 29681-29687.
Altiok, Soner, et al., PPARy induces cell cycle withdrawal: inhibition of E2F/DP DNA-binding activity via down-regulation of PP2A, Genes & Development 11:1987-1998, 1997.
Tontonoz, Peter, et al., "Terminal differentiation of human liposarcoma cells induced by ligands for peroxisome proliferator-activated receptor y and the retinoid X receptor", Proc. Natl, Acad. Sci. USA, vol. 94, pp. 237-241, Jan. 1997, Medical Sciences.

*Primary Examiner* — Samira Jean-Louis
(74) *Attorney, Agent, or Firm* — Calfee, Halter & Grisword LLP

(57) ABSTRACT

Bcl-xL/Bcl-2 binding inhibitors useful in the treatment of unwanted proliferating cells, including cancers and precancers, in subjects in need of such treatment. Also provided are methods of treating a subject having unwanted proliferating cells comprising administering a therapeutically effective amount of a Bcl-xL/Bcl-2 binding inhibitor described herein to a subject in need of such treatment. Also provided are methods of preventing the proliferation of unwanted proliferating cells, such as cancers and precancers, in a subject comprising the step of administering a therapeutically effective amount of a Bcl-xL/Bcl-2 binding inhibitor described herein to a subject at risk of developing a condition characterized by unwanted proliferating cells.

4 Claims, 8 Drawing Sheets

SMALL MOLECULE BCL-XL/BCL-2 BINDING INHIBITORS

CROSS-REFERENCE TO RELATED APPLICATIONS

This application is a divisional of prior U.S. application Ser. No. 11/315,077, filed Dec. 22, 2005 now U.S. Pat. No. 7,714,005, which claims priority to U.S. Provisional Patent Application No. 60/638,519 filed Dec. 22, 2004. Priority to both applications is hereby claimed, and the entire disclosures of both applications are incorporated herein by reference.

STATEMENT REGARDING FEDERALLY FUNDED RESEARCH

The present invention was funded, at least in part, by National Institutes of Health Grant CA-94829. The government may have certain rights in this invention.

BACKGROUND OF THE INVENTION

Thiazolidenediones (TZDs), including troglitazone (TG), rosiglitazone (RG), pioglitazone (PG), and ciglitazone (CG), are synthetic ligands of the peroxisome proliferator-activated receptor γ (PPARγ) (1). This family of PPARγ agonists improves insulin sensitivity by increasing transcription of certain insulin-sensitive genes involved in the metabolism and transport of lipids, thus representing a new class of oral antidiabetic agents. More recently, certain TZDs, especially TG and CG, have also been shown to inhibit the proliferation of many cancer cell lines that express high levels of PPARγ, including, but not limited to, those of colon, prostate, breast, and liposarcoma [review: (2)]. As PPARγ-mediated effects of TZDs promote the differentiation of preadipocytes, one school of thought attributes the same mechanism to the terminal differentiation and cell cycle arrest of tumor cells (3). However, the PPARγ-activated target genes that mediate the antiproliferative effects remain elusive, as genomic responses to PPARγ activation in cancer cells are highly complicated (4). Reported causal mechanisms include attenuated expression of protein phosphatase 2A (5), cyclins D1 and E, inflammatory cytokines and transcription factors (2), and increased expression of an array of gene products linked to growth regulation and cell maturation (4). On the other hand, several lines of evidence indicate that the inhibitory effect of TZDs on tumor cell proliferation was independent of PPARγ activation. For example, the antitumor effects appear to be structure-specific irrespective of potency in PPARγ activation, i.e., TG and CG are active while RG and PG are not. Also, there exists a three-orders-of-magnitude discrepancy between the concentration required to produce antitumor effects and that to mediate PPARγ activation. To date, an array of non-PPARγ targets have been implicated in the antitumor activities of TG and/or CG in different cell systems, which include intracellular $Ca^{2+}$ stores (6), phosphorylating activation of ERKs (extracellular signal-regulated kinases) (7, 8), JNK (c-Jun N-terminal protein kinase), and p38 (9), up-regulation of early growth response-1 (10), $p27^{kip1}$ (11), $p21^{WAF/CIP1}$ (12), p53, and Gadd45 (13), and altered expression of Bcl-2 family members (9). However, some of these targets appear to be cell type-specific due to differences in signaling pathways regulating cell growth and survival in different cell systems.

In light of the potential use of TZDs in prostate cancer prevention/treatment (14, 15), signaling mechanisms whereby these PPARγ agonists inhibit the proliferation of prostate cancer cells represent the focus of this investigation. We report here the development of novel TZD derivatives that lack activity in PPARγ activation but retain the ability to induce apoptosis in two prostate cancer cell lines with distinct PPARγ expression status, suggesting that these two pharmacological activities are unrelated. More importantly, we demonstrate that TZD-mediated apoptosis was attributable, in part, to the inhibition of the anti-apoptotic functions of Bcl-xL and Bcl-2 by disrupting the BH3 domain-mediated interactions with pro-apoptotic Bcl-2 members. From a translational perspective, dissociation of these two pharmacological activities, i.e., PPARγ activation and Bcl-xL/Bcl-2 inhibition, provides a molecular basis to use Δ2-TG as a scaffold to generate a novel class of Bcl-xL/Bcl-2 inhibitors. Accordingly, we developed a structurally optimized Δ2-TG derivative (TG-88) with high in vivo potency in inhibiting PC-3 tumor growth.

SUMMARY OF THE INVENTION

Provided are Bcl-xL/Bcl-2 binding inhibitors useful in the treatment of unwanted proliferating cells, including cancers and precancers, in subjects in need of such treatment. Also provided are methods of treating a subject having unwanted proliferating cells comprising administering a therapeutically effective amount of a compound described herein to a subject in need of such treatment. Also provided are methods of preventing the proliferation of unwanted proliferating cells, such as cancers and precancers, in a subject comprising the step of administering a therapeutically effective amount of a compound described herein to a subject at risk of developing a condition characterized by unwanted proliferating cells. In some embodiments, the compounds described herein reduce the proliferation of unwanted cells by inducing apoptosis in those cells. In one embodiment, the compounds described herein are used in the treatment of prostate cancer in a subject in need of such treatment. In another embodiment, the compounds described herein are used in a method of preventing prostate cancer in a subject, wherein the subject is at risk of developing prostate cancer. In some embodiments, the methods treating unwanted proliferating cells, including cancers and precancers, comprise inducing apoptosis in the unwanted proliferating cells by administering an effective amount of the Bcl-xL/Bcl-2 binding inhibitor to the subject in need of such treatment.

DETAILED DESCRIPTION OF THE INVENTION

Figure 1:
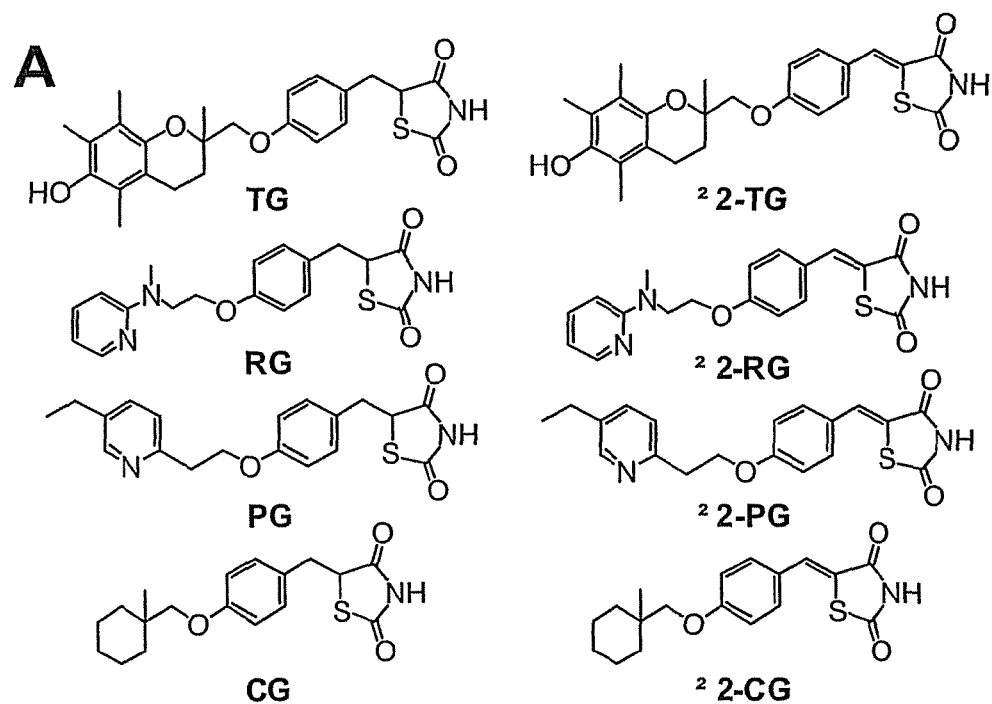
FIG. 1 Development of PPARγ-inactive TZD derivatives. (A) Chemical structures of TG, RG, PG, CG, and the respective Δ2-derivatives. (B) Δ-2-TZD derivatives lack activity in PPARγ activation. Analysis of PPARγ activation was carried out as described in the Materials and Methods. In brief, PC-3 cells were exposed to individual test agents (10 µM) or DMSO vehicle in 10% FBS-supplemented RPMI 1640 medium for 48 h. Amounts of activated PPARγ in the resulting nuclear extracts were analyzed by PPARγ transcription factor ELISA kit. Each data point represents mean±S.D. (n=3). *P<0.01.
Figure 1:
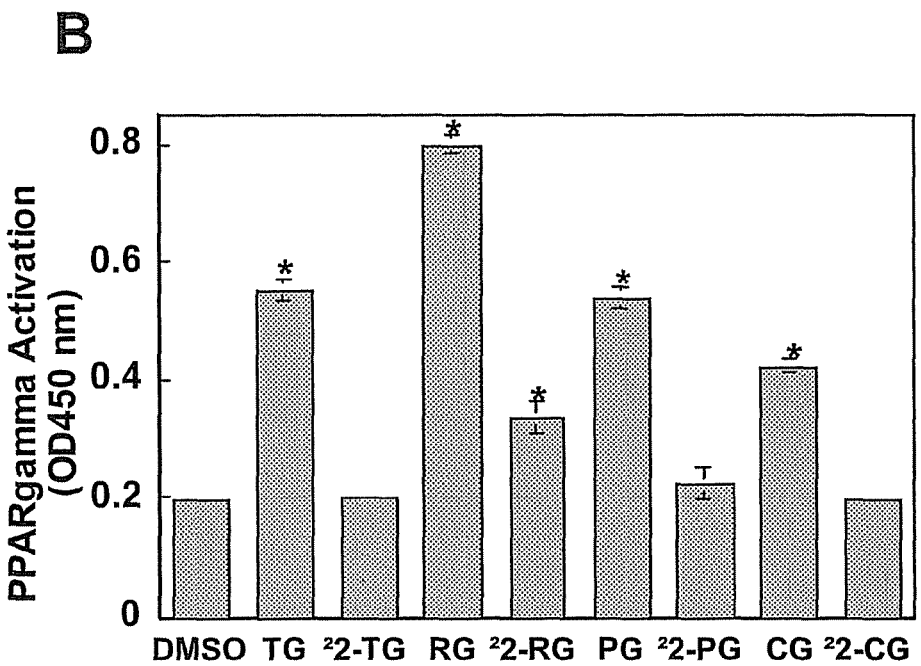

Provided are Bcl-xL/Bcl-2 binding inhibitors useful in the treatment of unwanted proliferating cells, including cancers and precancers, in subjects in need of such treatment. Also provided are methods of treating a subject having unwanted proliferating cells comprising administering a therapeutically effective amount of a compound described herein to a subject in need of such treatment. Also provided are methods of preventing the proliferation of unwanted proliferating cells, such as cancers and precancers, in a subject comprising the step of administering a therapeutically effective amount of a compound described herein to a subject at risk of developing a condition characterized by unwanted proliferating cells. In some embodiments, the compounds described herein reduce the proliferation of unwanted cells by inducing apoptosis in those cells. In one embodiment, the compounds described herein are used in the treatment of prostate cancer in a subject in need of such treatment. In another embodiment, the compounds described herein are used in a method of preventing prostate cancer in a subject, wherein the subject is at risk of developing prostate cancer. In some embodiments, the methods treating unwanted proliferating cells, including cancers and precancers, comprise inducing apoptosis in the unwanted proliferating cells by administering an effective amount of the Bcl-xL/Bcl-2 binding inhibitors described herein to the subject in need of such treatment.

In one embodiment the Bcl-xL/Bcl-2 binding inhibitors described herein have the following structure:

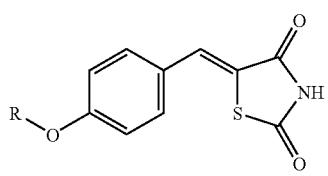

wherein R is selected from aryl, heteroaryl, cycloalkyl, heterocycloalkyl, alkylaryl, and combinations thereof; and wherein R may be substituted at one or more substitutable positions with a hydroxyl, or alkyl substituent. In some embodiments, R is selected from the group consisting of

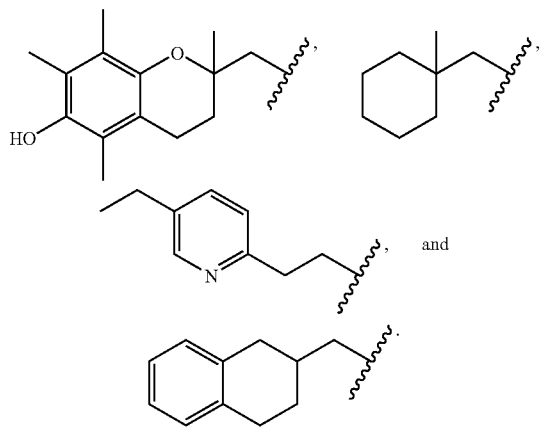

Some embodiments include:

TABLE 1

| Entry | compound | R | IC50 for MTT | IC50 for WB |
|---|---|---|---|---|
| 1 | Δ2-TG | | 57 | 22 |
| 2 | Δ2-CG | | 70 | 13 |
| 3 | Δ2-PG | | | |
| 4 | TG-15 | | 37 | 3.8 |

In another embodiment, the Bcl-xL/Bcl-2 binding inhibitors described herein have the following structure:

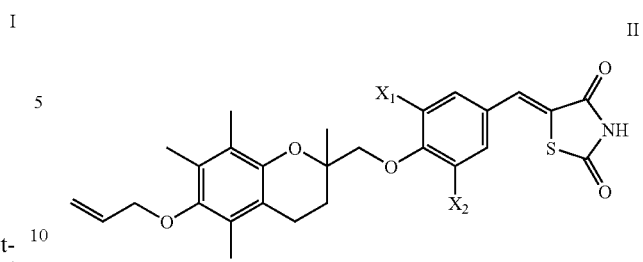

wherein $X_1$ is selected from the group consisting of H, alkyl, alkoxy, halo, nitro, and combinations thereof; and $X_2$ is selected from the group consisting of H, alkyl, alkoxy, halo, and combinations thereof. In some embodiments, $X_1$ is selected from H, Br, $CH_3$, $OCH_3$, $OCH_2CH_3$, $NO_2$, and Cl; and $X_2$ is selected from H, $CH_3$, $OCH_3$, and Br. Some embodiments include:

TABLE 2

| Entry | compound | X1 | X2 | IC50 for MTT | IC50 for WB |
|---|---|---|---|---|---|
| 5 | TG-6 | H | H | 9 | 3 |
| 6 | TG-27 | Br | H | 28 | >7.5 |
| 7 | TG-28 | OMe | H | 14.5 | 2.3 |
| 8 | TG-29 | Me | H | 23.5 | 3.6 |
| 9 | TG-52 | Me | Me | 10.5 | 7.5 |
| 10 | TG-54 | Br | OMe | 17.5 | 3.8 |
| 11 | TG-55 | OEt | H | 17 | >7.5 |
| 12 | | Br | Br | | |
| 13 | | $NO_2$ | H | | |
| 14 | | Cl | H | | |

In another embodiment, the Bcl-xL/Bcl-2 binding inhibitors described herein have the following structure:

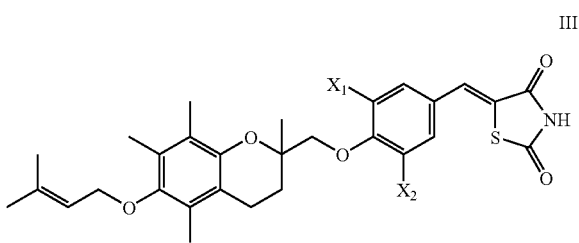

III wherein $X_1$ is selected from the group consisting of H, alkyl, alkoxy, halo, nitro, haloalkylaryl, haloaryl, alkylaryl, and combinations thereof.; and $X_2$ is selected from the group consisting of H, alkyl, alkoxy, halo, and combinations thereof. In some embodiments, $X_1$ is selected from the group consisting of H, methyl, methoxy, ethoxy, fluoro, chloro, bromo, nitro, trifluoromethylphenyl, fluorophenyl, and ethylphenyl; and $X_2$ is selected from the group consisting of H, methyl, methoxy, and bromo. Some embodiments are shown in the table below.

TABLE 3

| Entry | compound | X1 | X2 | IC50 for MTT | IC50 for WB |
|---|---|---|---|---|---|
| 15 | TG-14 | H | H | 14.5 | 7 |
| 16 | TG-16 | OMe | H | 15 | 5.6 |
| 17 | TG-17 | Me | H | 14.5 | 3.2 |
| 18 | TG-30 | F | H | 12.5 | 7.2 |
| 19 | TG-31 | 4-CF3-phenyl | H | >50 | >7.5 |
| 20 | TG-32 | 4-F-phenyl | H | 19.5 | >7.5 |
| 21 | TG-33 | 4-ethyl-phenyl | H | >50 | >7.5 |
| 22 | TG-34 | Br | Br | 15.5 | 2.7 |
| 23 | TG-35 | N2O | H | 38 | 2.7 |
| 24 | TG-44 | Br | OMe | 14.5 | >7.5 |
| 25 | TG-45 | OEt | H | 13 | 6.7 |
| 26 | TG-88 | Br | H | 14.5 | >7.5 |
| 27 |  | Me | Me |  |  |
| 28 |  | Cl | H |  |  |

In another embodiment, the Bcl-xL/Bcl-2 binding inhibitors described herein have the following structure:

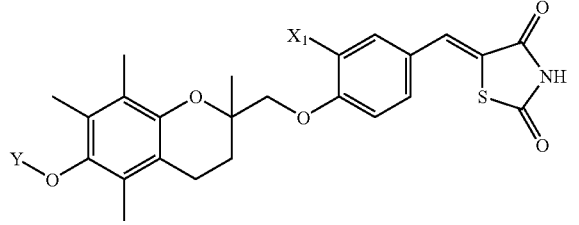

IV wherein $X_1$ is selected from the group consisting of H, halo, and combinations thereof and Y is selected from the group consisting of alkylaryl, ankenylaryl, alkenyl, ester carboxylic acids, ester alcohols, and combinations thereof. In some embodiments, $X_1$ is selected from the group consisting of H and Br, and Y is selected from the group consisting of

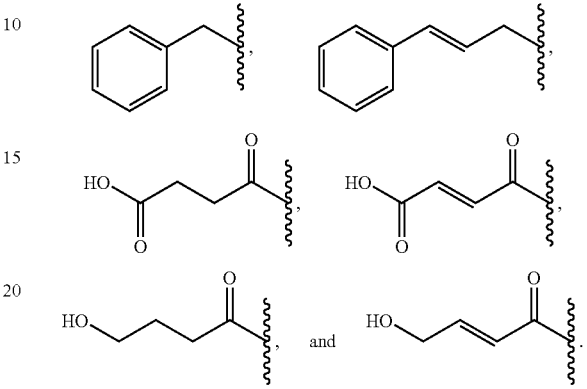

Some embodiments are shown in the table below.

TABLE 4

| Entry | compound | X1 | Y | IC50 for MTT | IC50 for WB |
|---|---|---|---|---|---|
| 29 | TG-10 | H | cinnamyl | 19 | >7.5 |
| 30 | TG-11 | Br | cinnamyl | 28.5 | >7.5 |
| 31 | TG-12 | H | benzyl | 16.67 | 3.6 |
| 32 | TG-13 | H | HOOC-CH2CH2-C(O)- | >50 | >7.5 |
| 33 |  | Br | HOOC-CH2CH2-C(O)- |  |  |
| 34 |  | H | HOOC-CH=CH-C(O)- |  |  |

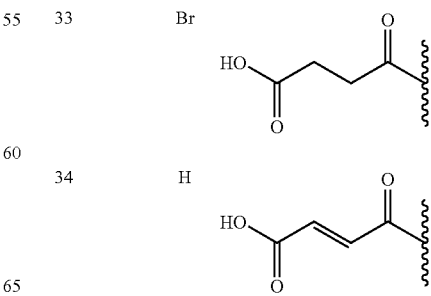

TABLE 4-continued

| Entry | compound | X1 | Y | IC50 for MTT | IC50 for WB |
|---|---|---|---|---|---|
| 35 | | Br | HO-C(=O)-CH=CH-C(=O)- | | |
| 36 | | H | HO-CH2CH2CH2-C(=O)- | | |
| 37 | | Br | HO-CH2CH2CH2-C(=O)- | | |
| 38 | | Br | HO-CH2-CH=CH-C(=O)- | | |

In another embodiment, the Bcl-xL/Bcl-2 binding inhibitors described herein have the following structure:

V

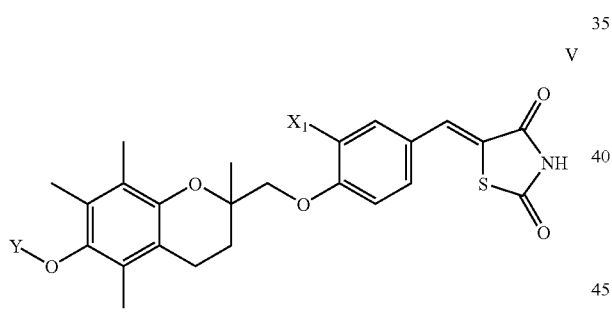

wherein $X_1$ is selected from the group consisting of H, halo, and combinations thereof; and Y is selected from the group consisting of straight-chain alkenyl, branched alkenyl, and combinations thereof. Some specific embodiments include:

TABLE 5

| Entry | compound | X1 | Y | IC50 for MTT | IC50 for WB |
|---|---|---|---|---|---|
| 39 | TG-3 | H | CH2=CH-CH2-CH2- | 11 | 3.5 |
| 40 | TG-89 | Br | (CH3)2C=CH-CH2- | | |

In another embodiment, the Bcl-xL/Bcl-2 binding inhibitors described herein have the following structure:

VI

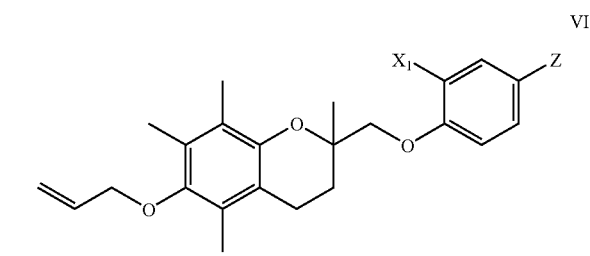

wherein $X_1$ is selected from the group consisting of H, alkoxy, halo, and combinations thereof; and Z is selected from the group consisting of

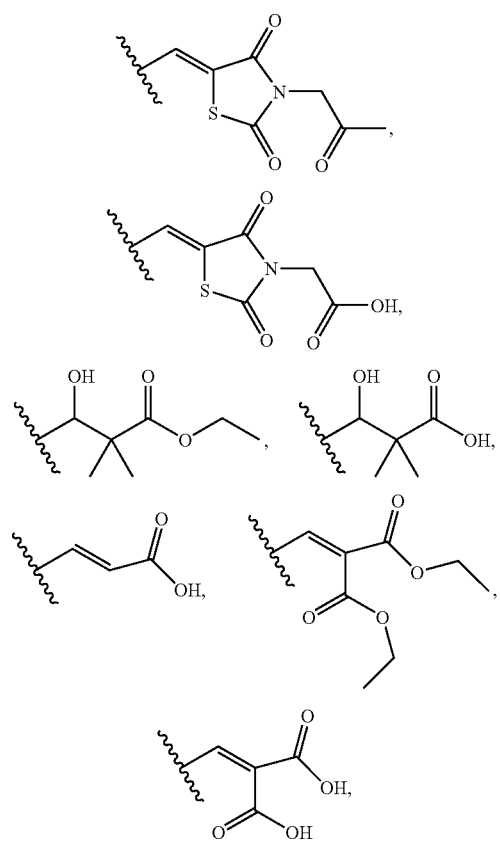

and combinations thereof. Some specific embodiments include:

TABLE 6
| Entry | compound | X1 | Z | IC50 for MTT | IC50 for WB |
|---|---|---|---|---|---|
| 41 | TG-9 | H | 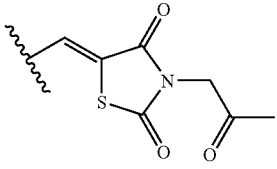 | >50 | >7.5 |
| 42 | | H | 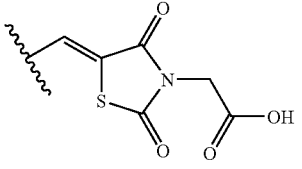 | | |
| 43 | | OMe | 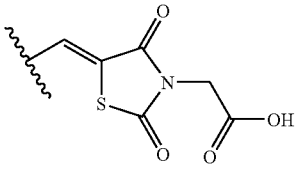 | | |
| 44 | | OEt | 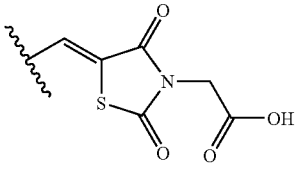 | | |
| 45 | | H | 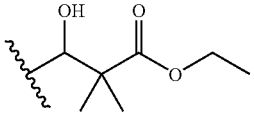 | | |
| 46 | | OMe | 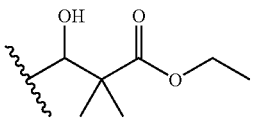 | | |
| 47 | | OEt | 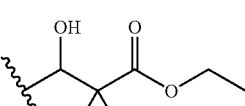 | | |
| 48 | | H | 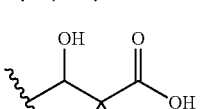 | | |
| 49 | | OMe | 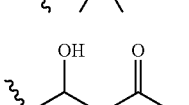 | | |
| 50 | | OEt | 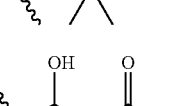 | | |
| 51 | | H | 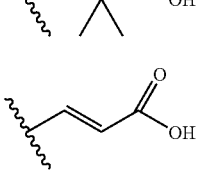 | | |

In another embodiment, the Bcl-xL/Bcl-2 binding inhibitors described herein have the following structure:

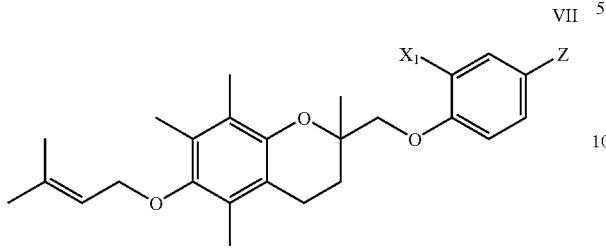

VII wherein $X_1$ is selected from the group consisting of H, halo, and combinations thereof and Z is selected from the group consisting of

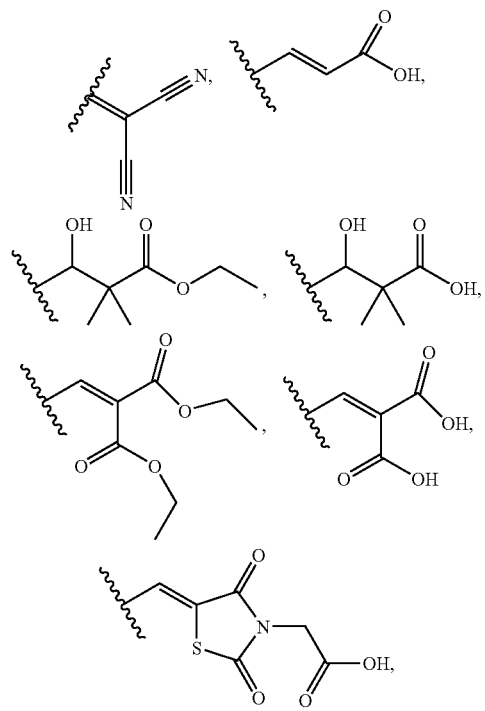

and combinations thereof. Some specific embodiments are shown in the table below:

TABLE 7

| Entry | compound | $X_1$ | Z | IC50 for MTT | IC50 for WB |
|---|---|---|---|---|---|
| 60 | TG-36 | Br | (dicyanovinyl) | >50 | >7.5 |
| 61 | TG-37 | Br | (acrylic acid) | 34 | >7.5 |
| 62 | TG-38 | Br | (hydroxy dimethyl ethyl ester) | >50 | 4.5 |
| 63 | TG-39 | Br | (hydroxy dimethyl acid) | 46 | >7.5 |
| 64 | TG-41 | Br | (diethyl malonate vinyl) | >50 | >7.5 |

TABLE 7-continued

| Entry | compound | X1 | Z | IC50 for MTT | IC50 for WB |
|---|---|---|---|---|---|
| 65 | TG-42 | Br | (malonic acid vinyl group) | >50 | >7.5 |
| 66 | | H | (2,4-dioxothiazolidin-3-yl acetic acid methylene) | | |
| 67 | | Br | (2,4-dioxothiazolidin-3-yl acetic acid methylene) | | |
| 68 | | Cl | (2,4-dioxothiazolidin-3-yl acetic acid methylene) | | |

In another embodiment, the Bcl-xL/Bcl-2 binding inhibitors described herein have the following structure:

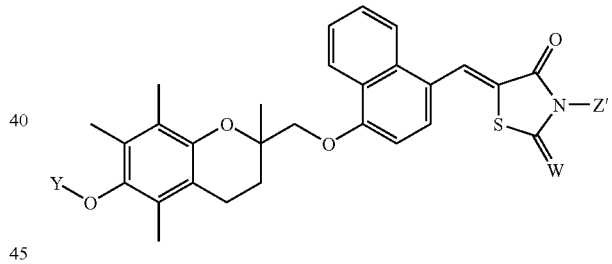

VIII wherein W is selected from O, S and combinations thereof; Y is selected from straight chain alkenyl, branched alkenyl and combinations thereof; and Z' is selected from H and carboxylic acid. Some specific embodiments are shown in the table below:

TABLE 8

| Entry | compound | W | Y | Z' | IC50 for MTT | IC50 for WB |
|---|---|---|---|---|---|---|
| 69 | TG-43 | O | (3-methylbut-2-enyl) | H | 14.5 | 7.2 |
| 70 | TG-46 | S | (3-methylbut-2-enyl) | H | 37.33 | 6.7 |
| 71 | TG-53 | O | (but-3-enyl) | H | 14.5 | 3.4 |

TABLE 8-continued

| Entry | compound | W | Y | Z' | IC50 for MTT | IC50 for WB |
|---|---|---|---|---|---|---|
| 72 | | O | 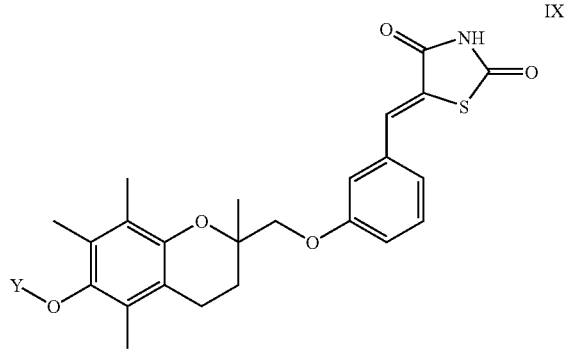 | | | |

In another embodiment, the Bcl-xL/Bcl-2 binding inhibitors described herein have the following structure:

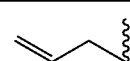

IX wherein Y is selected from straight chain alkenyl, branched alkenyl and combinations thereof. Some specific embodiments are shown in the table below:

TABLE 9

| Entry | compound | Y | IC50 for MTT | IC50 for WB |
|---|---|---|---|---|
| 73 | TG-51 | 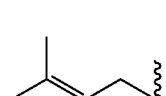 | 40 | 4.4 |
| 74 | | 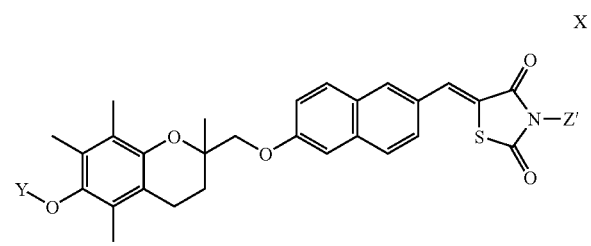 | | |

In another embodiment, the Bcl-xL/Bcl-2 binding inhibitors described herein have the following structure:

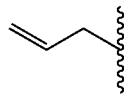

X wherein Y is selected from straight chain alkenyl, branched alkenyl and combinations thereof, and Z' is selected from H and carboxylic acid. Some specific embodiments are shown in the table below:

TABLE 10

| Entry | Y | Z' |
|---|---|---|
| 75 | 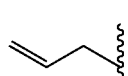 | H |
| 76 |  | 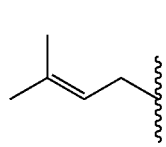 |
| 77 | 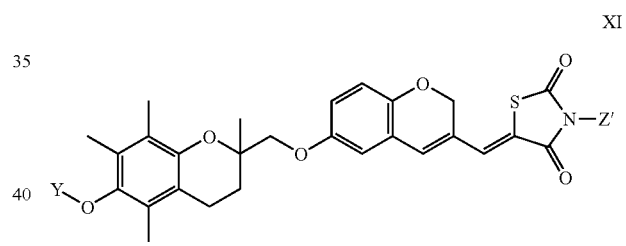 | H |

In another embodiment, the Bcl-xL/Bcl-2 binding inhibitors described herein have the following structure:

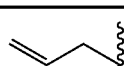

XI wherein Y is selected from straight chain alkenyl, branched alkenyl and combinations thereof, and Z' is selected from H and carboxylic acid. Some specific embodiments are shown in the table below:

TABLE 11

| Entry | Y | Z' |
|---|---|---|
| 78 |  | H |
| 79 |  | 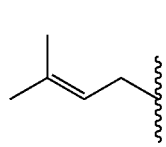 |
| 80 |  | H |

Abbreviations used herein: PPARγ, peroxisome proliferator-activated receptor γ; TZDs, thiazolidenediones; TG, troglitazone; CG, ciglitazone; RG, rosiglitazone; PG, pioglitazone; Δ2-TG, 5-[4-(6-hydroxy-2,5,7,8-tetramethyl-chroman-2-ylmethoxy)-benzylidene]-2,4-thiazolidinedione; Δ2-RG, 5-[4-(1-methyl-cyclohexylmethoxy)-benzylidene]-thiazolidine-2,4-dione, Δ2-RG, 5-{4-[2-(methyl-pyridin-2-yl-amino)-ethoxy]-benzylidene}-thiazolidine-2,4-dione, 5-{4-[2-(5-ethyl-pyridin-2-yl)-ethoxy]-benzylidene}-thiazolidine-2,4-dione; FBS, fetal bovine serum; MTT, [3-(4,5-dimethylthiazol-2-yl)-2,5-diphenyl-2H-tetrazolium bromide]; FP, fluorescence polarization.

As used herein, the term "prevention" includes either preventing the onset of a clinically evident unwanted cell proliferation altogether or preventing the onset of a preclinically evident stage of unwanted rapid cell proliferation in individuals at risk. Also intended to be encompassed by this definition is the prevention of metastasis of malignant cells or to arrest or reverse the progression of malignant cells. This includes prophylactic treatment of those at risk of developing precancers and cancers.

The terms "therapeutically effective" and "pharmacologically effective" are intended to qualify the amount of each agent which will achieve the goal of improvement in disease severity and the frequency of incidence over treatment of each agent by itself, while avoiding adverse side effects typically associated with alternative therapies.

The term "subject" for purposes of treatment includes any human or animal subject who has a disorder characterized by unwanted, rapid cell proliferation. Such disorders include, but are not limited to cancers and precancers. For methods of prevention the subject is any human or animal subject, and preferably is a human subject who is at risk of obtaining a disorder characterized by unwanted, rapid cell proliferation, such as cancer. The subject may be at risk due to exposure to carcinogenic agents, being genetically predisposed to disorders characterized by unwanted, rapid cell proliferation, and so on. Besides being useful for human treatment, the compounds of the present invention are also useful for veterinary treatment of mammals, including companion animals and farm animals, such as, but not limited to dogs, cats, horses, cows, sheep, and pigs. In most embodiments, subject means a human.

The phrase "pharmaceutically acceptable salts" connotes salts commonly used to form alkali metal salts and to form addition salts of free acids or free bases. The nature of the salt is not critical, provided that it is pharmaceutically acceptable. Suitable pharmaceutically acceptable acid addition salts of compounds of formulae I and II may be prepared from an inorganic acid or from an organic acid. Examples of such inorganic acids are hydrochloric, hydrobromic, hydroiodic, nitric, carbonic, sulfuric, and phosphoric acid. Appropriate organic acids may be selected from aliphatic, cycloaliphatic, aromatic, araliphatic, heterocyclic, carboxylic, and sulfonic classes of organic acids, examples of which include formic, acetic, propionic, succinic, glycolic, gluconic, lactic, malic, tartaric, citric, ascorbic, glucoronic, maleic, fumaric, pyruvic, aspartic, glutamic, benzoic, anthranilic, mesylic, salicylic, p-hydroxybenzoic, phenylacetic, mandelic, ambonic, pamoic, methanesulfonic, ethanesulfonic, benzenesulfonic, pantothenic, 2-hydroxyethanesulfonic, toluenesulfonic, sulfanilic, cyclohexylaminosulfonic, stearic, algenic, β-hydroxybutyric, galactaric, and galacturonic acids. Suitable pharmaceutically acceptable base addition salts of the compounds described herein include metallic salts made from aluminum, calcium, lithium, magnesium, potassium, sodium, and zinc. Alternatively, organic salts made from N,N'-dibenzylethylenediamine, chloroprocaine, choline, diethanolamine, ethylenediamine, meglumine (N-methylglucamine) and procaine may be used form base addition salts of the compounds described herein. All of these salts may be prepared by conventional means from the corresponding compounds described herein by reacting, for example, the appropriate acid or base with the compound.

Where the term alkyl is used, either alone or with other terms, such as haloalkyl or alkylaryl, it includes $C_1$ to $C_{10}$ linear or branched alkyl radicals, examples include methyl, ethyl, propyl, isopropyl, butyl, tert-butyl, and so forth. The term "haloalkyl" includes $C_1$ to $C_{10}$ linear or branched alkyl radicals substituted with one or more halo radicals. Some examples of haloalkyl radicals include trifluoromethyl, 1,2-dichloroethyl, 3-bromopropyl, and so forth. The term "halo" includes radicals selected from F, Cl, Br, and I. Alkyl radical substituents of the present invention may also be substituted with other groups such as azido, for example, azidomethyl, 2-azidoethyl, 3-azidopropyl and so on.

The term aryl, used alone or in combination with other terms such as alkylaryl, haloaryl, or haloalkylaryl, includes such aromatic radicals as phenyl, biphenyl, and benzyl, as well as fused aryl radicals such as naphthyl, anthryl, phenanthrenyl, fluorenyl, and indenyl and so forth. The term "aryl" also encompasses "heteroaryls," which are aryls that have carbon and one or more heteroatoms, such as O, N, or S in the aromatic ring. Examples of heteroaryls include indolyl, pyrrolyl, and so on. "Alkylaryl" or "arylalkyl" refers to alkyl-substituted aryl groups such as butylphenyl, propylphenyl, ethylphenyl, methylphenyl, 3,5-dimethylphenyl, tert-butylphenyl and so forth. "Haloaryl" refers to aryl radicals in which one or more substitutable positions has been substituted with a halo radical, examples include fluorophenyl, 4-chlorophenyl, 2,5-chlorophenyl and so forth. "Haloalkylaryl" refers to aryl radicals that have a haloalkyl substituent.

Provided are pharmaceutical compositions for ablating cyclin D1 in MCF-7 cells specifically. These compounds are also useful for treating, preventing, or delaying the onset of a cancer in a subject in need of such treatment. The pharmaceutical composition comprises a therapeutically effective amount of a compound disclosed herein, or a derivative or pharmaceutically acceptable salt thereof, in association with at least one pharmaceutically acceptable carrier, adjuvant, or diluent (collectively referred to herein as "carrier materials") and, if desired, other active ingredients. The active compounds of the present invention may be administered by any suitable route known to those skilled in the art, preferably in the form of a pharmaceutical composition adapted to such a route, and in a dose effective for the treatment intended. The active compounds and composition may, for example, be administered orally, intra-vascularly, intraperitoneally, intranasal, intrabronchial, subcutaneously, intramuscularly or topically (including aerosol). With some subjects local administration, rather than system administration, may be preferred. Formulation in a lipid vehicle may be used to enhance bioavailability.

The administration of the present invention may be for either prevention or treatment purposes. The methods and compositions used herein may be used alone or in conjunction with additional therapies known to those skilled in the art in the prevention or treatment of disorders characterized by unwanted, rapid proliferation of cells. Alternatively, the methods and compositions described herein may be used as adjunct therapy. By way of example, the compounds of the present invention may be administered alone or in conjunction with other antineoplastic agents or other growth inhibiting agents or other drugs or nutrients, as in an adjunct therapy.

The phrase "adjunct therapy" or "combination therapy" in defining use of a compound described herein and one or more other pharmaceutical agents, is intended to embrace administration of each agent in a sequential manner in a regimen that will provide beneficial effects of the drug combination, and is intended as well to embrace co-administration of these agents in a substantially simultaneous manner, such as in a single formulation having a fixed ratio of these active agents, or in multiple, separate formulations for each agent.

For the purposes of combination therapy, there are large numbers of antineoplastic agents available in commercial use, in clinical evaluation and in pre-clinical development, which could be selected for treatment of cancers or other disorders characterized by rapid proliferation of cells by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents. Alternatively, other anti-neoplastic agents, such as metallomatrix proteases inhibitors (MMP), such as MMP-13 inhibitors, or $\beta_v\beta_3$ inhibitors may be used. Suitable agents which may be used in combination therapy will be recognized by those of skill in the art. Similarly, when combination therapy is desired, radioprotective agents known to those of skill in the art may also be used.

When preparing the compounds described herein for oral administration, the pharmaceutical composition may be in the faun of, for example, a tablet, capsule, suspension or liquid. The pharmaceutical composition is preferably made in the faun of a dosage unit containing a particular amount of the active ingredient. Examples of such dosage units are capsules, tablets, powders, granules or a suspension, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethyl-cellulose; and with lubricants such as talc or magnesium stearate. The active ingredient may also be administered by injection as a composition wherein, for example, saline, dextrose or water may be used as a suitable carrier.

For intravenous, intramuscular, subcutaneous, or intraperitoneal administration, the compound may be combined with a sterile aqueous solution which is preferably isotonic with the blood of the recipient. Such formulations may be prepared by dissolving solid active ingredient in water containing physiologically compatible substances such as sodium chloride, glycine, and the like, and having a buffered pH compatible with physiological conditions to produce an aqueous solution, and rendering said solution sterile. The formulations may be present in unit or multi-dose containers such as sealed ampoules or vials.

For treating cancers or other unwanted proliferative cells that are localized in the G.I. tract, the compound may be formulated with acid-stable, base-labile coatings known in the art which begin to dissolve in the high pH small intestine. Formulation to enhance local pharmacologic effects and reduce systemic uptake are preferred.

Formulations suitable for parenteral administration conveniently comprise a sterile aqueous preparation of the active compound which is preferably made isotonic. Preparations for injections may also be formulated by suspending or emulsifying the compounds in non-aqueous solvent, such as vegetable oil, synthetic aliphatic acid glycerides, esters of higher aliphatic acids or propylene glycol.

The dosage form and amount can be readily established by reference to known treatment or prophylactic regiments. The amount of therapeutically active compound that is administered and the dosage regimen for treating a disease condition with the compounds and/or compositions of this invention depends on a variety of factors, including the age, weight, sex, and medical condition of the subject, the severity of the disease, the route and frequency of administration, and the particular compound employed, the location of the unwanted proliferating cells, as well as the pharmacokinetic properties of the individual treated, and thus may vary widely. The dosage will generally be lower if the compounds are administered locally rather than systemically, and for prevention rather than for treatment. Such treatments may be administered as often as necessary and for the period of time judged necessary by the treating physician. One of skill in the art will appreciate that the dosage regime or therapeutically effective amount of the inhibitor to be administered may need to be optimized for each individual. The pharmaceutical compositions may contain active ingredient in the range of about 0.1 to 2000 mg, preferably in the range of about 0.5 to 500 mg and most preferably between about 1 and 200 mg. A daily dose of about 0.01 to 100 mg/kg body weight, preferably between about 0.1 and about 50 mg/kg body weight, may be appropriate. The daily dose can be administered in one to four doses per day.

Several embodiments of the Bcl-xL/Bcl-2 inhibitors described herein, along with IC$_{50}$ values for Bcl-xL/Bak, Bcl-2/Bak and PC3 cells are shown in Table 12, below.

TABLE 12

| Entry | cmpd. | IC$_{50}$ Bcl-xl/Bak | IC$_{50}$ Bcl-2/Bak | IC$_{50}$ (μM) PC3 | structure |
|---|---|---|---|---|---|
| 1 | A2-TG | 18 ± 1 | 18 ± 1 | 20 ± 2 | 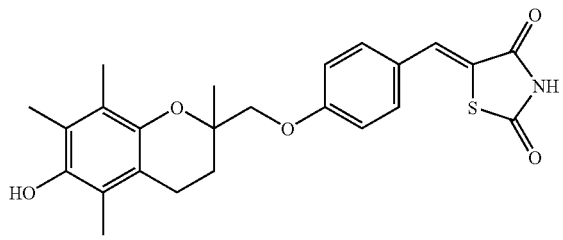 |

TABLE 12-continued

| Entry | cmpd. | IC$_{50}$ Bcl-xl/Bak | IC$_{50}$ Bcl-2/Bak | IC$_{50}$ (μM) PC3 | structure |
|---|---|---|---|---|---|
| 2 | Δ2-CG | 17 ± 2 | 22 ± 3 | 15 ± 1.2 | 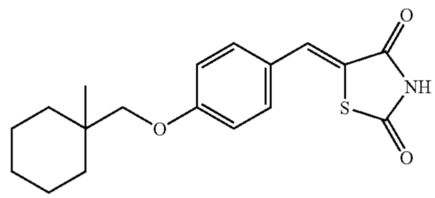 |
| 3 | Δ2-PG | >50 | >50 | >50 | 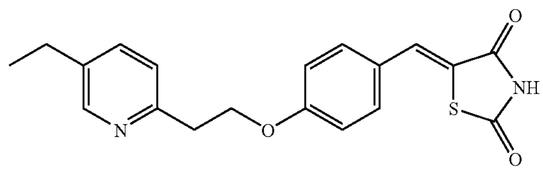 |
| 4 | TG-6 | 6.0 ± 0.5 | 5.5 ± 0.4 | 11 ± 0.8 | 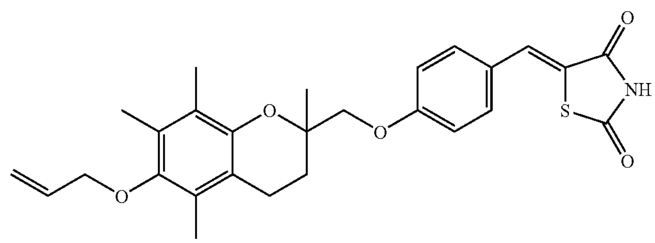 |
| 5 | TG-3 | 4.8 ± 0.5 | 7.3 ± 0.3 | 10 ± 1.2 | 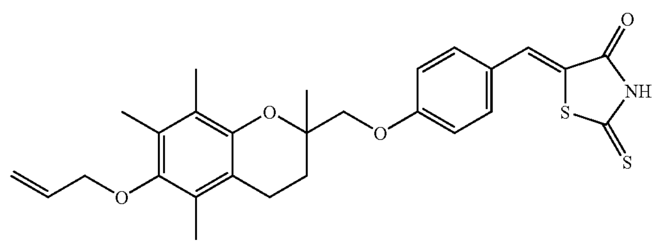 |
| 6 | TG-9 | >50 | >50 | >50 | 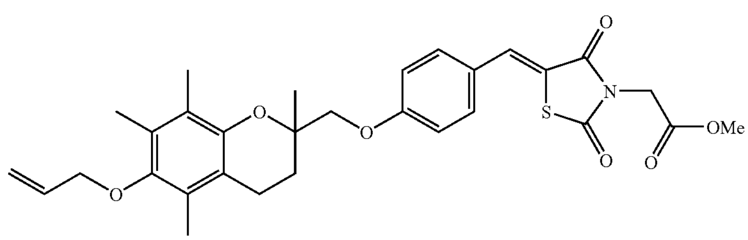 |
| 7 | TG-10 | 13 ± 0.9 | 19 ± 0.8 | 19 ± 0.5 | 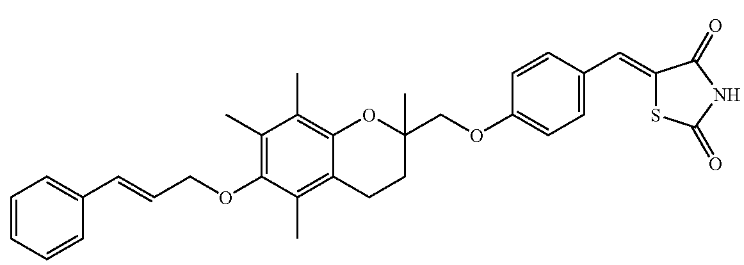 |

TABLE 12-continued

| Entry | cmpd. | IC$_{50}$ Bcl-xl/Bak | IC$_{50}$ Bcl-2/Bak | IC$_{50}$ (μM) PC3 | structure |
|---|---|---|---|---|---|
| 8 | TG-11 | 2.2 ± 0.2 | 3.1 ± 0.4 | 6 ± 0.3 | 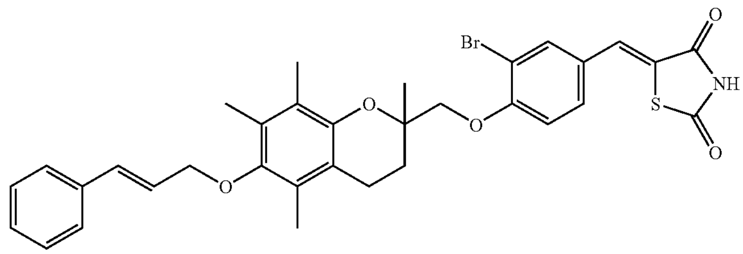 |
| 9 | TG-12 | 14 ± 1.1 | 18 ± 0.9 | 18 ± 1.3 | 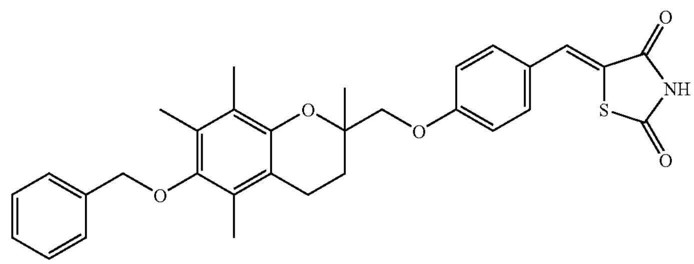 |
| 10 | TG-13 | 28 ± 1.4 | 30 ± 1.5 | 22 ± 0.6 | 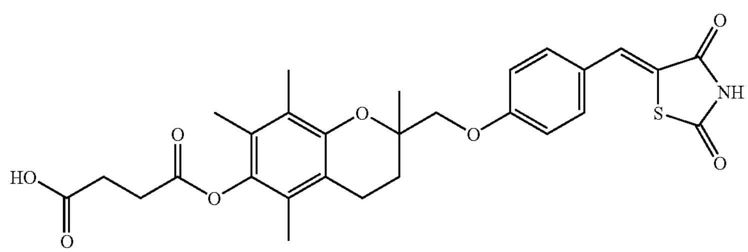 |
| 11 | TG-14 | 4.5 ± 0.4 | 4.8 ± 0.4 | 9 ± 1.0 | 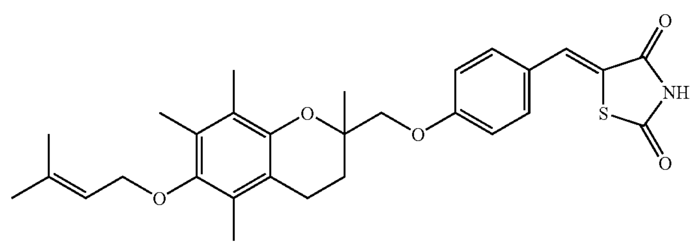 |
| 12 | TG-15 | 16 ± 0.5 | 18 ± 0.9 | 12 ± 0.9 | 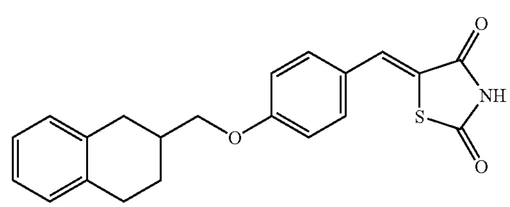 |
| 13 | TG-16 | 6.5 ± 0.5 | 4.8 ± 0.5 | 4.7 ± 0.2 | 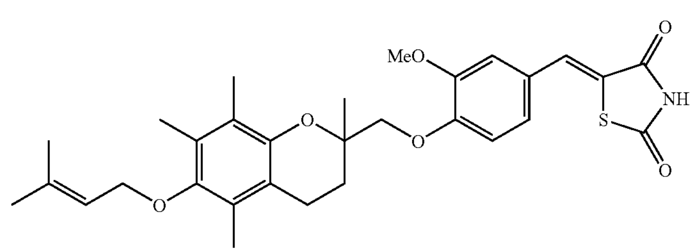 |

TABLE 12-continued
| Entry | cmpd. | IC$_{50}$ Bcl-xl/Bak | IC$_{50}$ Bcl-2/Bak | IC$_{50}$ (μM) PC3 | structure |
|---|---|---|---|---|---|
| 14 | TG-17 | 2.6 ± 0.3 | 3.1 ± 0.4 | 4.8 ± 0.3 | 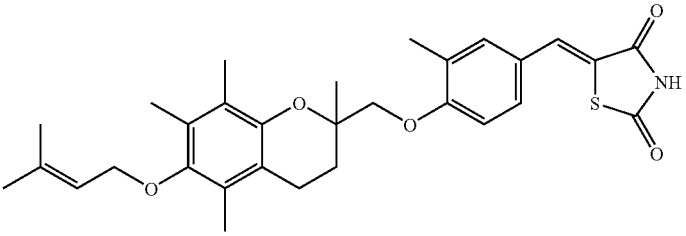 |
| 15 | TG-27 | 2.1 ± 0.2 | 2.7 ± 0.4 | 5.0 ± 0.5 | 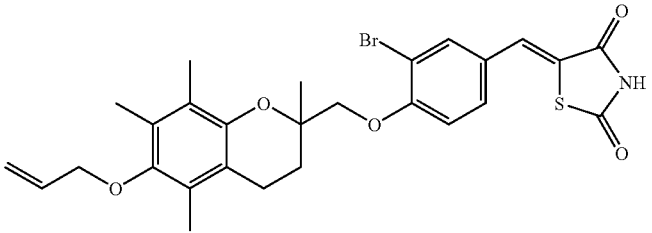 |
| 16 | TG-28 | 4.0 ± 0.3 | 4.4 ± 0.3 | 5.2 ± 0.5 | 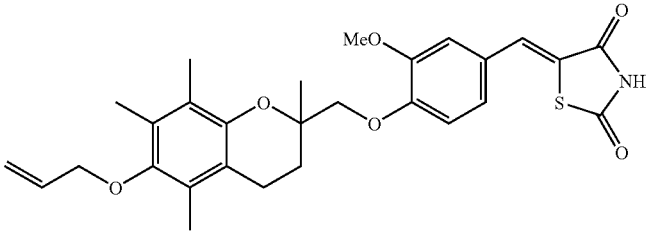 |
| 17 | TG-29 | 3.0 ± 0.3 | 3.5 ± 0.6 | 5.1 ± 0.4 | 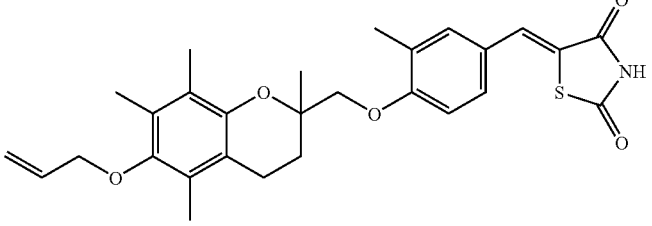 |
| 18 | TG-30 | 2.7 ± 0.3 | 3.4 ± 0.5 | 6.0 ± 0.4 | 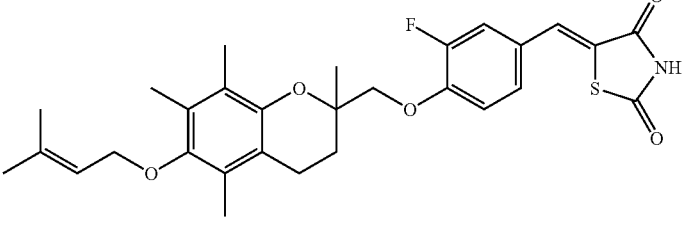 |
| 19 | TG-31 | 4.9 ± 1.2 | 4.7 ± 2.0 | 30 ± 1.1 | 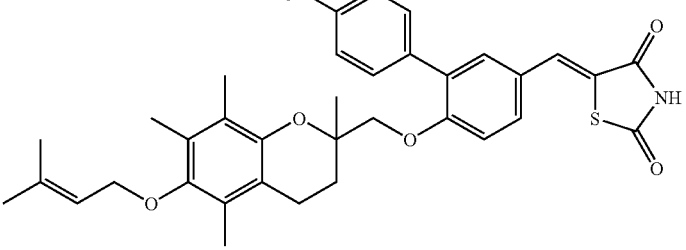 |

TABLE 12-continued

| Entry | cmpd. | IC$_{50}$ Bcl-xl/Bak | IC$_{50}$ Bcl-2/Bak | IC$_{50}$ (μM) PC3 | structure |
| --- | --- | --- | --- | --- | --- |
| 20 | TG-32 | 6.5 ± 0.5 | 6.6 ± 0.6 | 5.0 ± 0.4 | 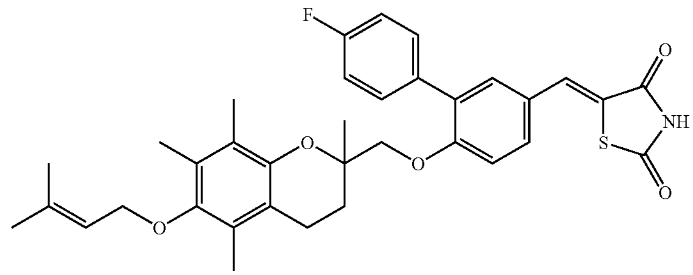 |
| 21 | TG-33 | 18 ± 0.8 | 21 ± 1.4 | 17 ± 0.9 | 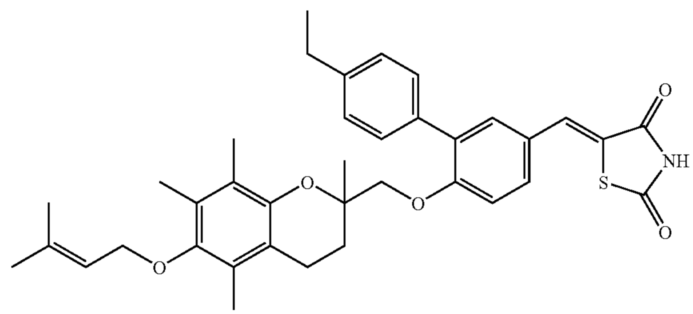 |
| 22 | TG-34 | 2.0 ± 0.2 | 2.8 ± 0.4 | 4.4 ± 0.4 | 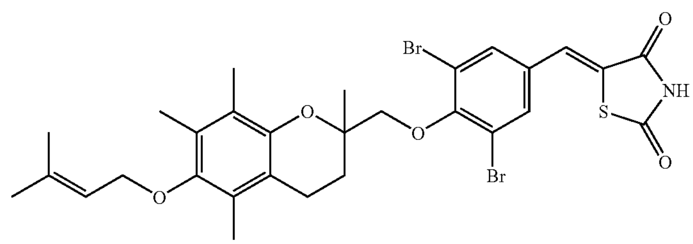 |
| 23 | TG-35 | | | >50 | 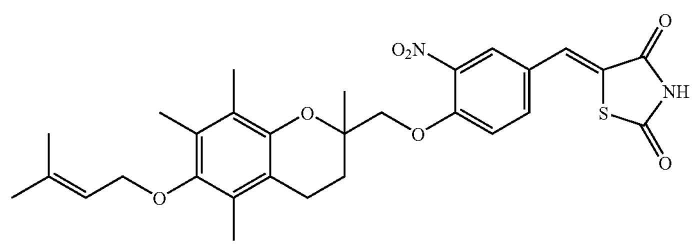 |
| 24 | TG-36 | | | >50 | 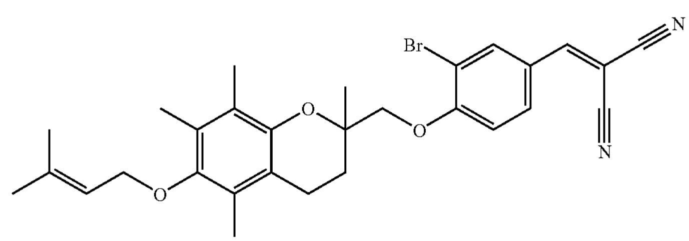 |
| 25 | TG-37 | | | 6 ± 0.7 | 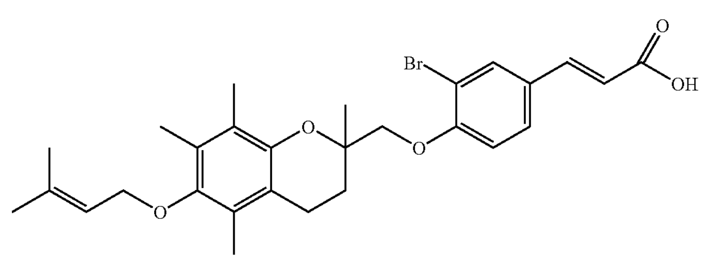 |

TABLE 12-continued

| Entry | cmpd. | IC$_{50}$ Bcl-xl/Bak | IC$_{50}$ Bcl-2/Bak | IC$_{50}$ (μM) PC3 | structure |
|---|---|---|---|---|---|
| 26 | TG-38 | | | 12.5 ± 0.6 | 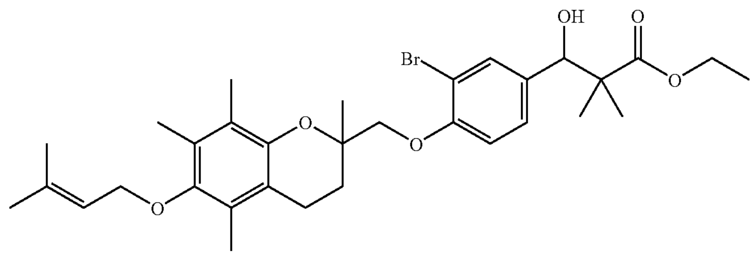 |
| 27 | TG-39 | | | 7 ± 0.4 | 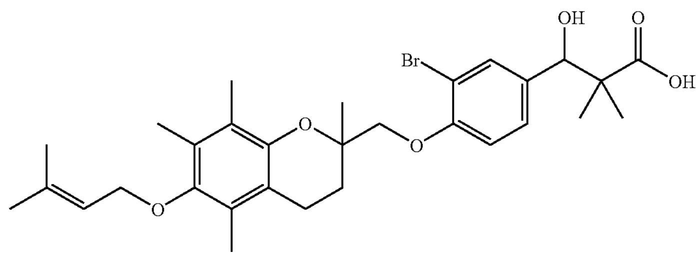 |
| 28 | TG-41 | | | >50 | 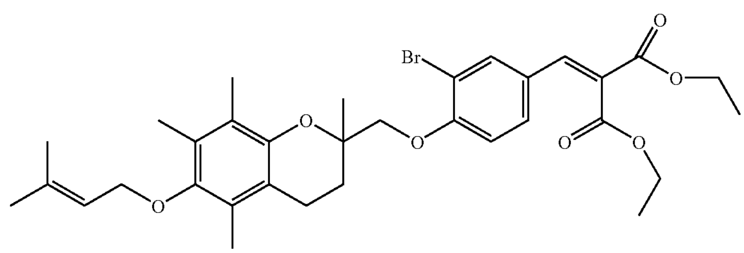 |
| 29 | TG-42 | | | 16 ± 0.3 | 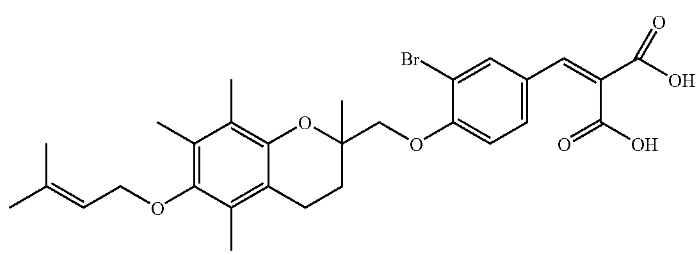 |
| 30 | TG-43 | | | 3.0 ± 0.2 | 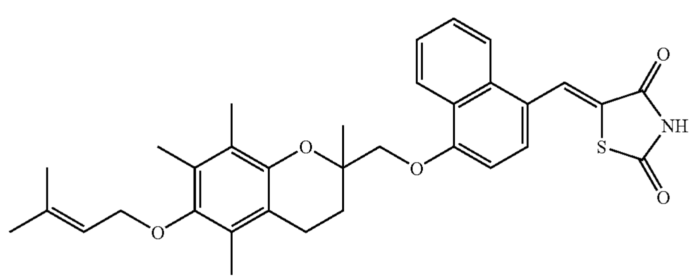 |
| 31 | TG-44 | | | 5.1 ± 0.4 | 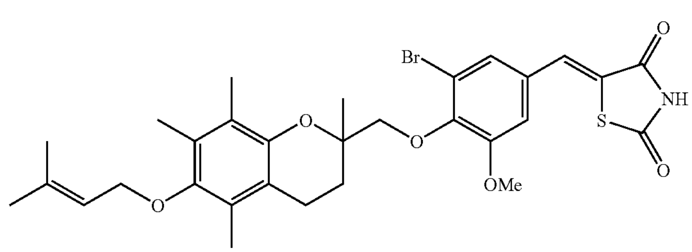 |

TABLE 12-continued

| Entry | cmpd. | IC$_{50}$ Bcl-xl/Bak | IC$_{50}$ Bcl-2/Bak | IC$_{50}$ (μM) PC3 | structure |
|---|---|---|---|---|---|
| 32 | TG-45 | | | 4.6 ± 0.3 | 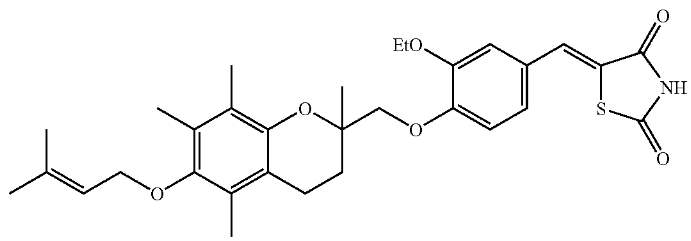 |
| 33 | TG-46 | | | 5.3 ± 0.3 | 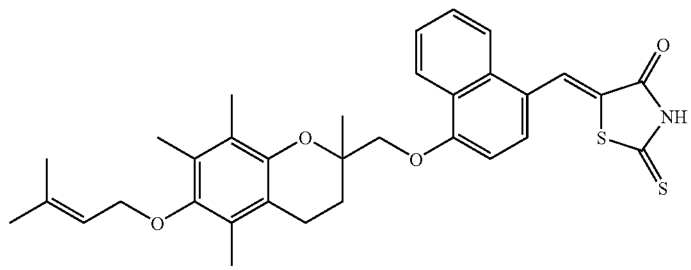 |
| 34 | TG-51 | | | 6.8 ± 0.2 | 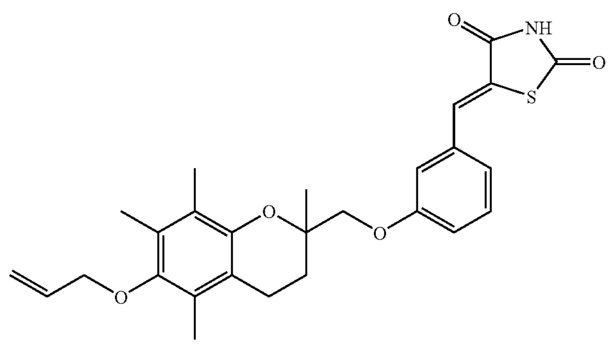 |
| 35 | TG-52 | | | 4.5 ± 0.2 | 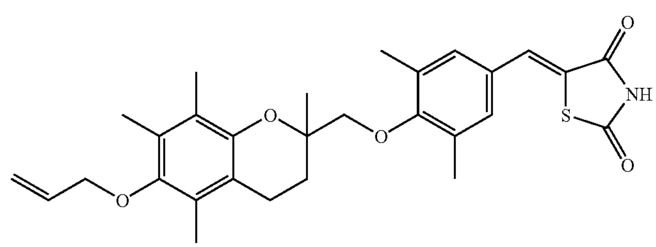 |
| 36 | TG-53 | | | 3.3 ± 0.3 | 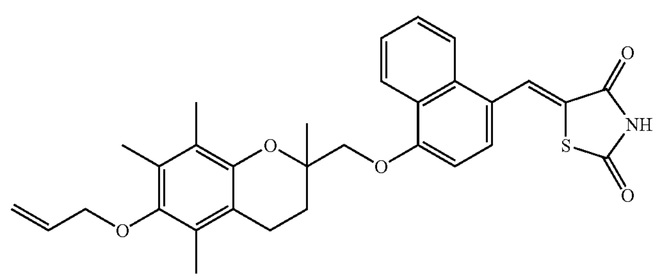 |

TABLE 12-continued

| Entry | cmpd. | IC$_{50}$ Bcl-xl/Bak | IC$_{50}$ Bcl-2/Bak | IC$_{50}$ (μM) PC3 | structure |
|---|---|---|---|---|---|
| 37 | TG-54 | | | | 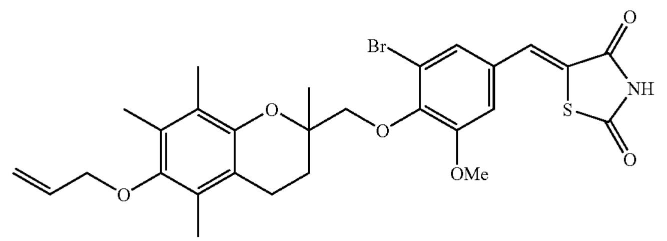 |
| 38 | TG-55 | | | | 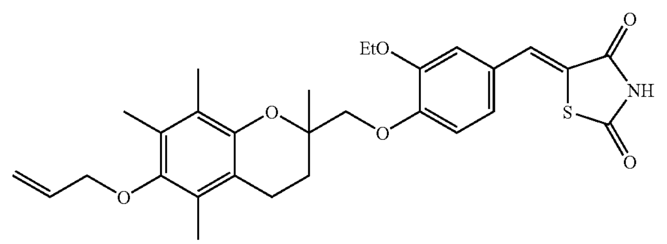 |
| 39 | TG-88 | 1.8 ± 0.2 | 2.8 ± 0.3 | 4.2 ± 0.2 | 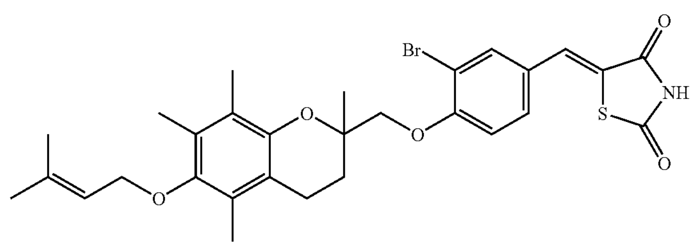 |
| 40 | TG-89 | | | 4.4 ± 0.4 | 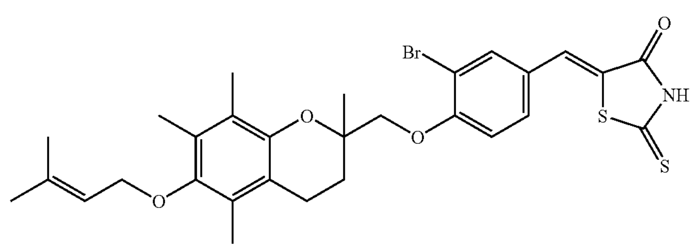 |
| 41 | | | | | 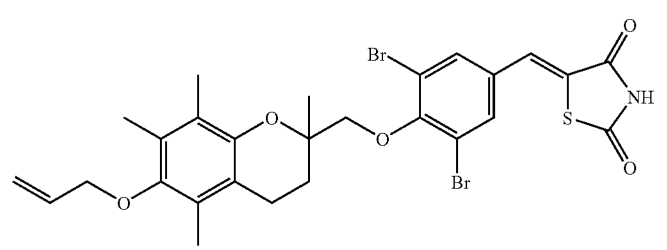 |
| 42 | | | | | 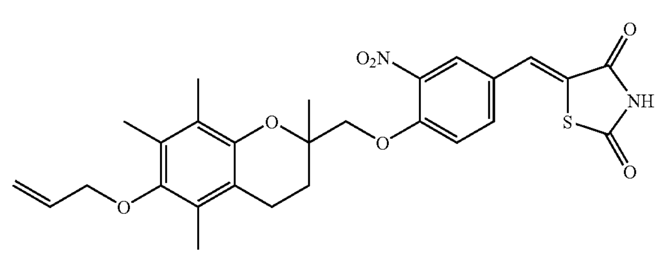 |

TABLE 12-continued
| Entry | cmpd. | IC$_{50}$ Bcl-xl/Bak | IC$_{50}$ Bcl-2/Bak | IC$_{50}$ (μM) PC3 | structure |
|---|---|---|---|---|---|
| 43 | | | | | 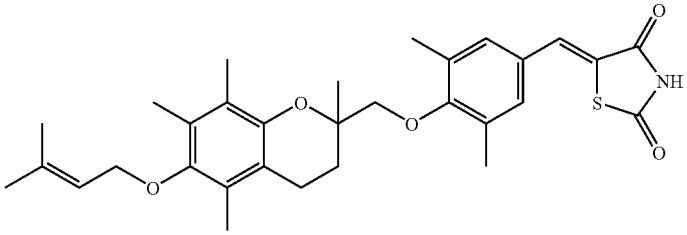 |
| 44 | | | | | 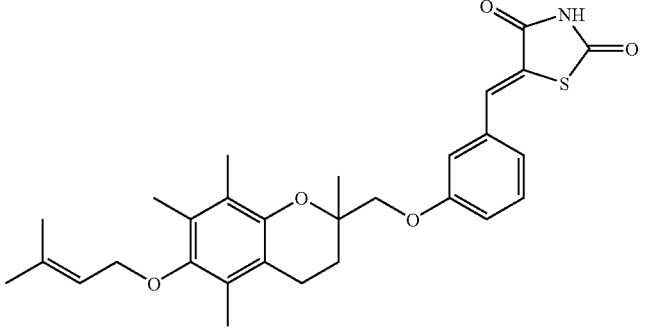 |
| 45 | | | | | 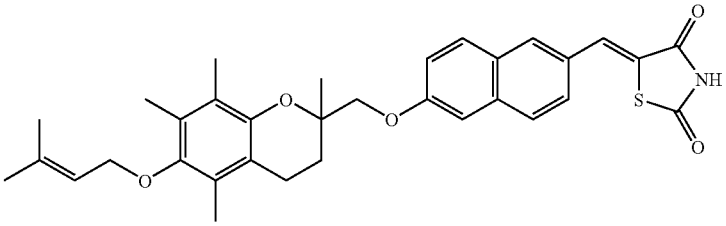 |
| 46 | | | | | 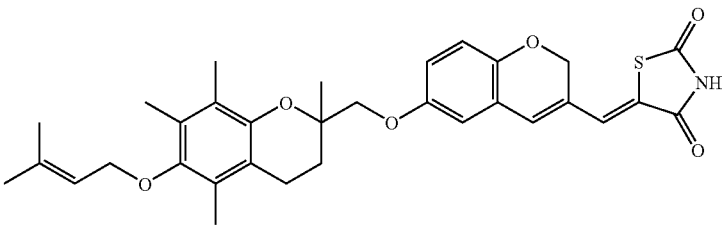 |
| 47 | | | | | 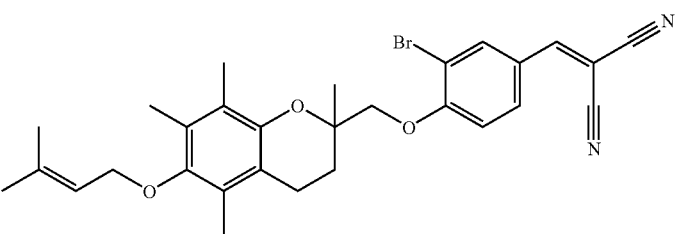 |
| 48 | | | | | 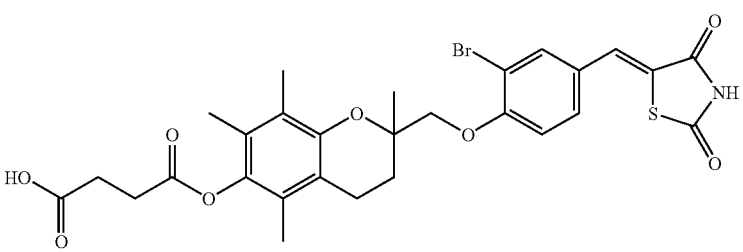 |

TABLE 12-continued

| Entry | cmpd. | IC$_{50}$ Bcl-xl/Bak | IC$_{50}$ Bcl-2/Bak | IC$_{50}$ (μM) PC3 | structure |
|---|---|---|---|---|---|
| 49 | | | | | 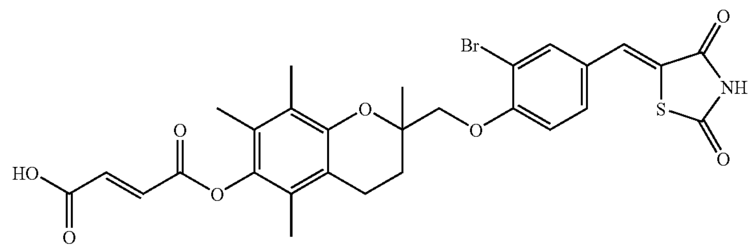 |
| 50 | | | | | 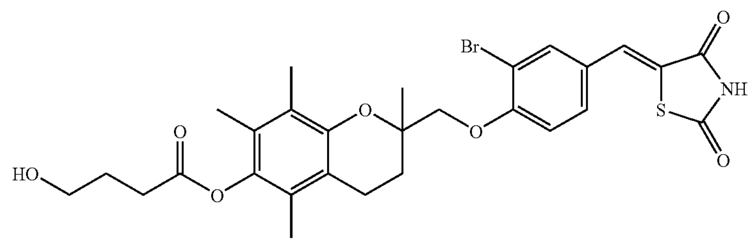 |
| 51 | | | | | 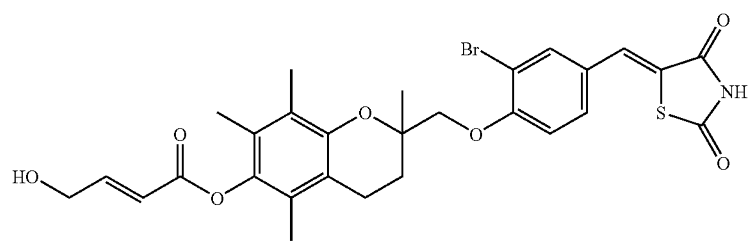 |
| 52 | | | | | 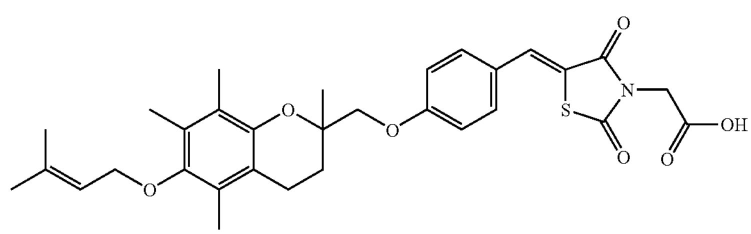 |
| 53 | | | | | 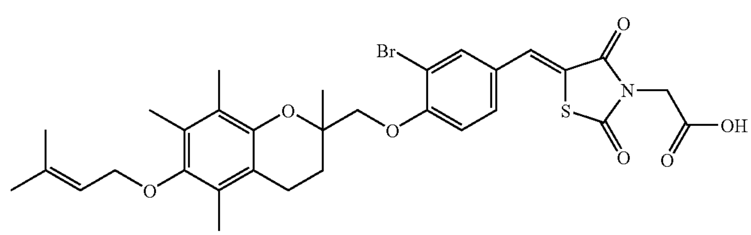 |
| 54 | | | | | 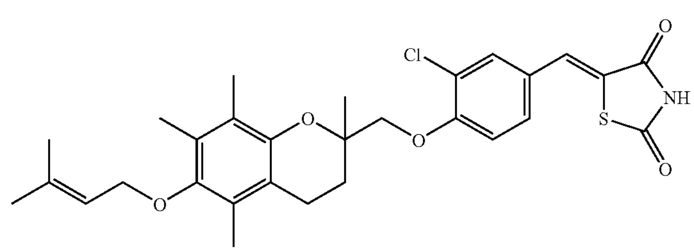 |

TABLE 12-continued

| Entry cmpd. | IC$_{50}$ Bcl-xl/Bak | IC$_{50}$ Bcl-2/Bak | IC$_{50}$ (µM) PC3 | structure |
|---|---|---|---|---|
| 55 | | | | 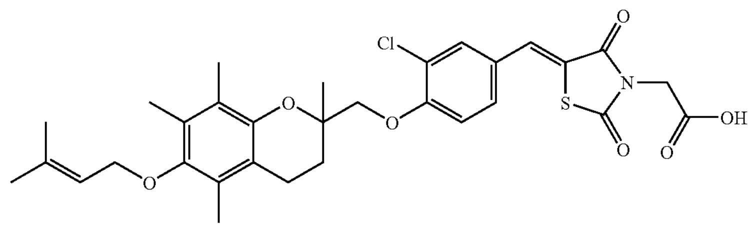 |
| 56 | | | | 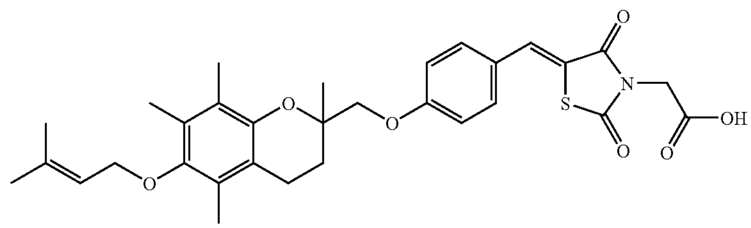 |
| 57 | | | | 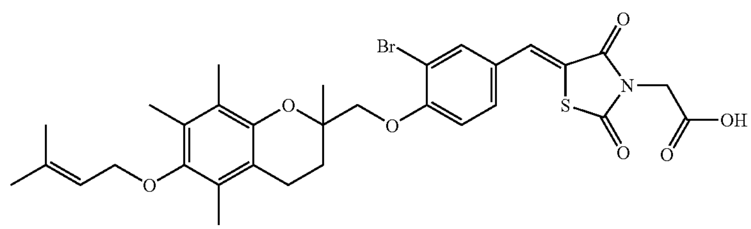 |
| 58 | | | | 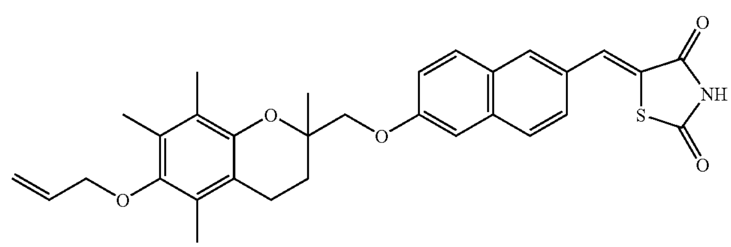 |
| 59 | | | | 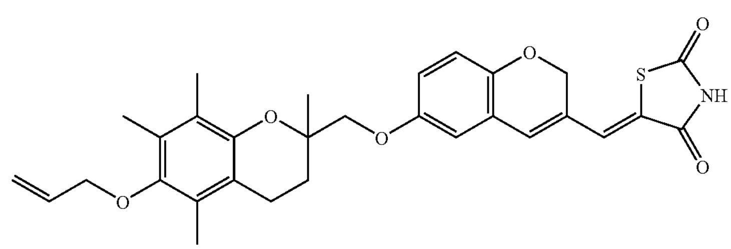 |
| 60 | | | | 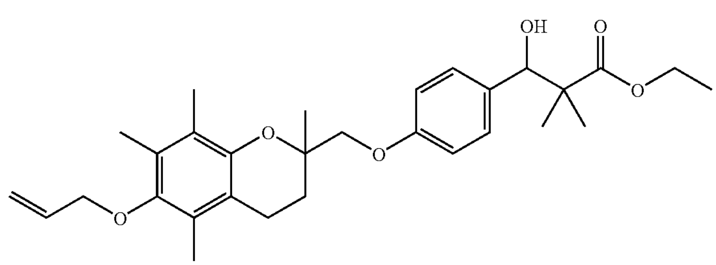 |

TABLE 12-continued

| Entry cmpd. | IC$_{50}$ Bcl-xl/Bak | IC$_{50}$ Bcl-2/Bak | IC$_{50}$ (µM) PC3 | structure |
|---|---|---|---|---|
| 61 | | | | 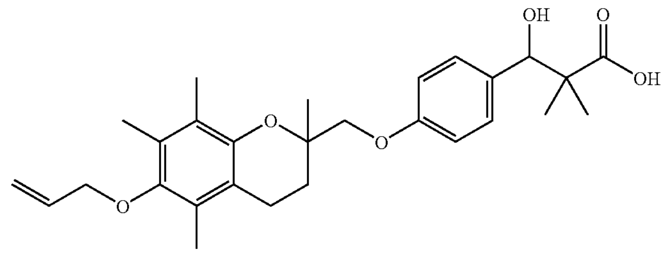 |
| 62 | | | | 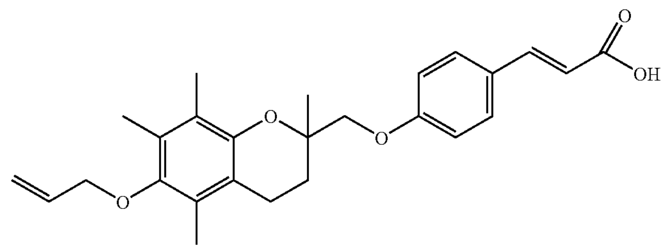 |
| 63 | | | | 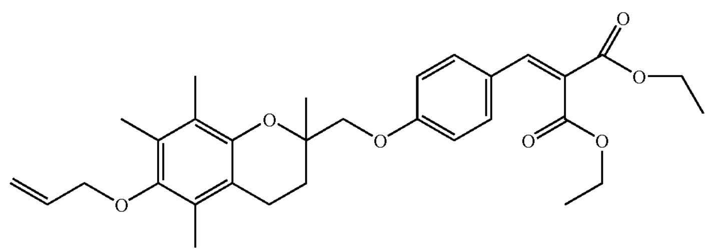 |
| 64 | | | | 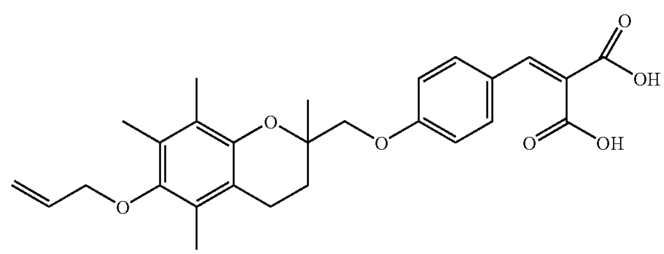 |
| 65 | | | | 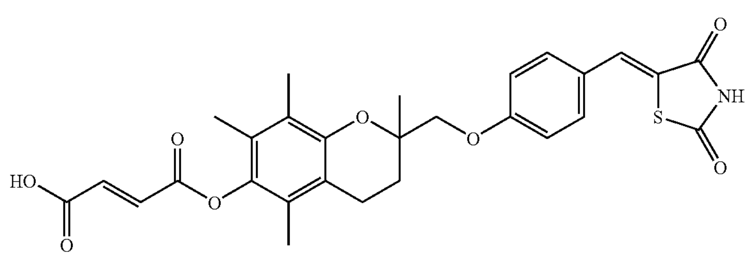 |
| 66 | | | | 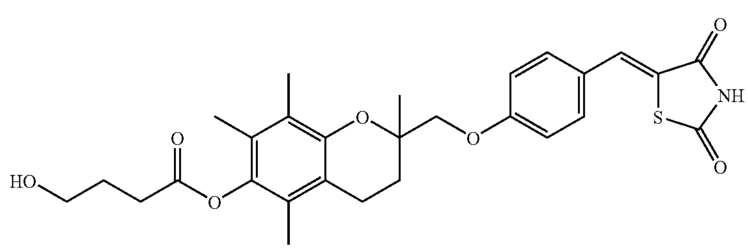 |

TABLE 12-continued

| Entry | cmpd. | IC$_{50}$ Bcl-xl/Bak | IC$_{50}$ Bcl-2/Bak | IC$_{50}$ (μM) PC3 | structure |
|---|---|---|---|---|---|
| 67 | | | | | 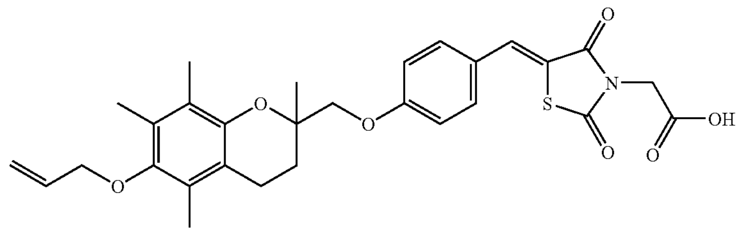 |
| 68 | | | | | 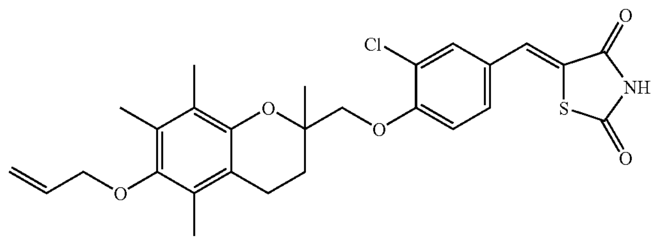 |
| 69 | | | | | 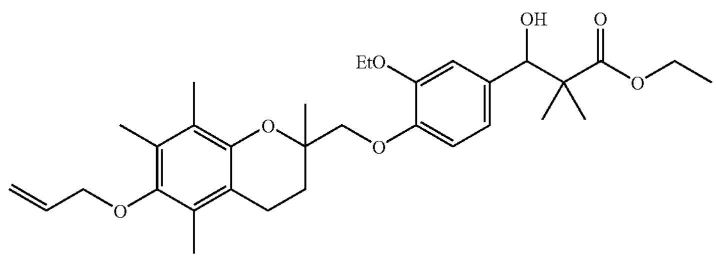 |
| 70 | | | | | 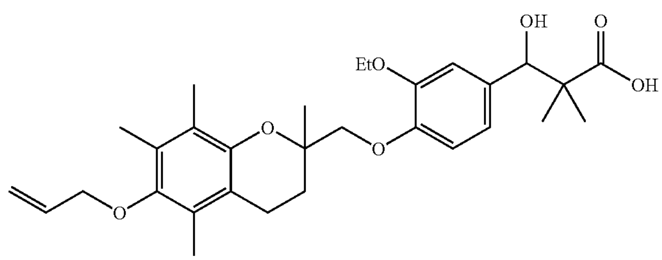 |
| 71 | | | | | 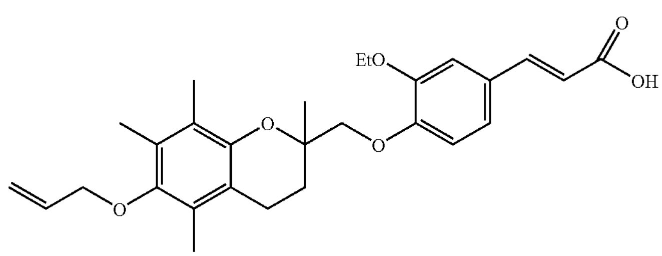 |
| 72 | | | | | 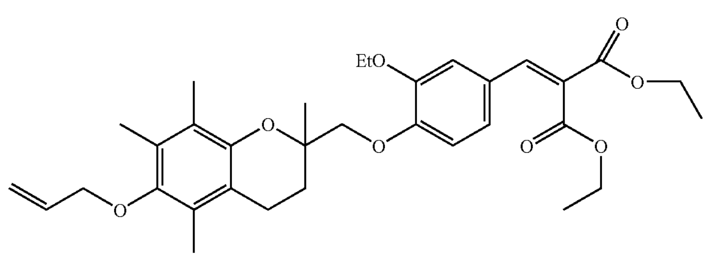 |

TABLE 12-continued

| Entry cmpd. | IC$_{50}$ Bcl-xl/Bak | IC$_{50}$ Bcl-2/Bak | IC$_{50}$ (μM) PC3 | structure |
|---|---|---|---|---|
| 73 | | | | 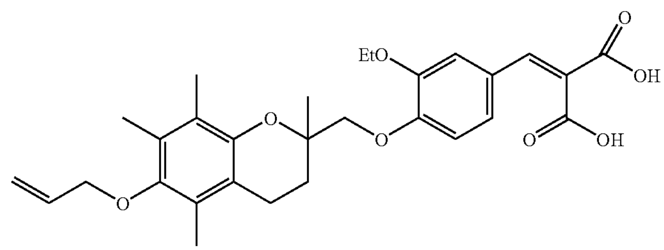 |
| 74 | | | | 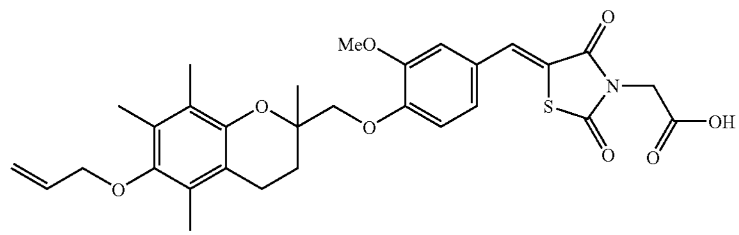 |
| 75 | | | | 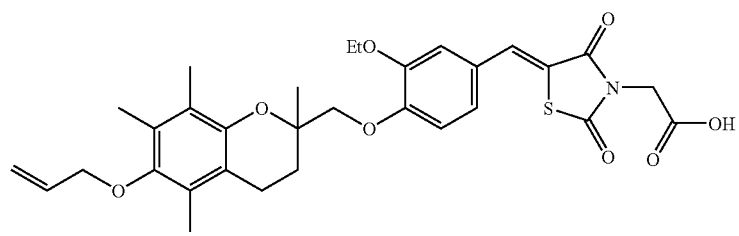 |
| 76 | | | | 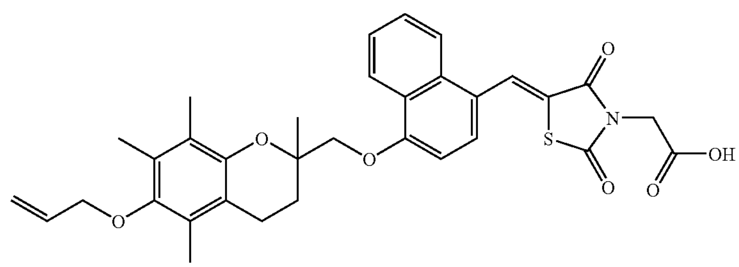 |
| 77 | | | | 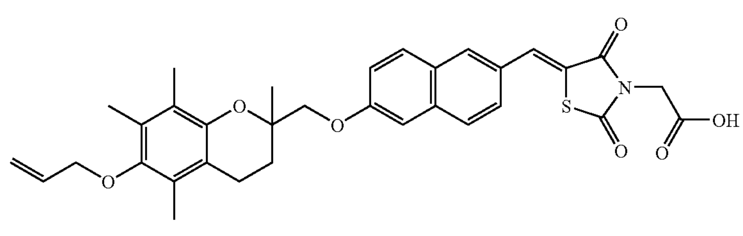 |
| 78 | | | | 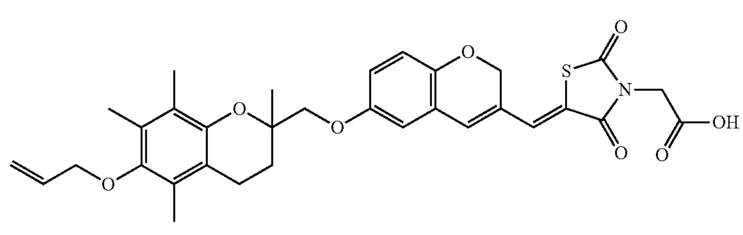 |

TABLE 12-continued

| Entry | cmpd. | IC$_{50}$ Bcl-xl/Bak | IC$_{50}$ Bcl-2/Bak | IC$_{50}$ (μM) PC3 | structure |
|---|---|---|---|---|---|
| 79 | | | | | 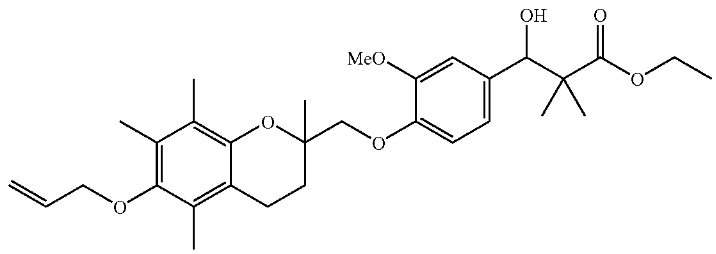 |
| 80 | | | | | 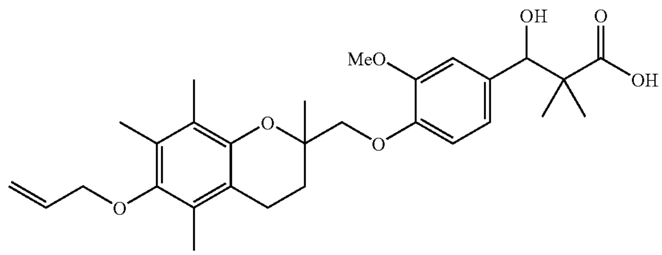 |
| 81 | | | | | 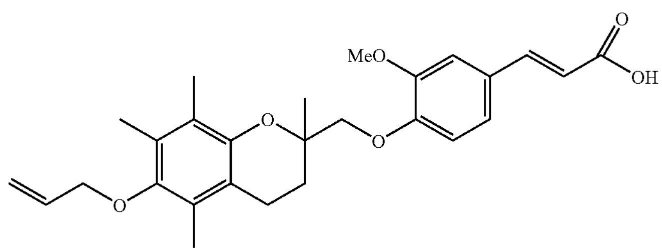 |
| 82 | | | | | 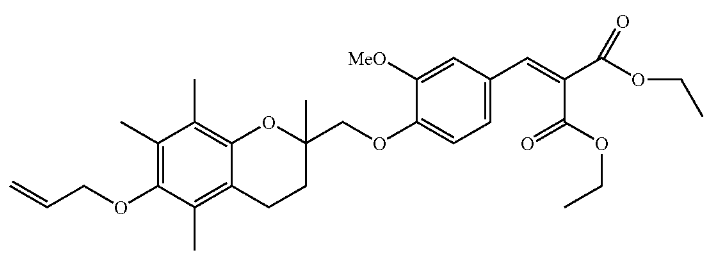 |
| 83 | | | | | 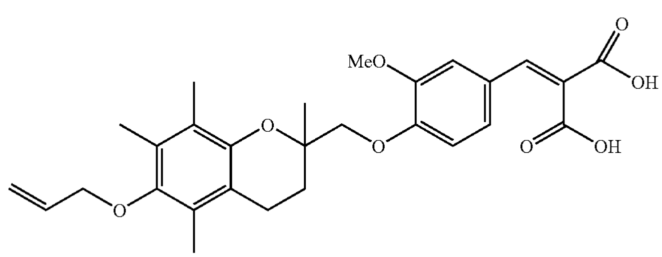 |

Materials and Methods

Reagents. Troglitazone (TG) and ciglitazone (CG) were purchased from Sigma (St. Louis, Mo.) and Cayman Chemical (Ann Arbor, Mich.), respectively. Rosiglitazone (RG) and pioglitazone (PG) were prepared from the respective commercial capsules by solvent extraction followed by recrystallization or chromatographic purification. Δ2-TG {5-[4-(6-hydroxy-2,5,7,8-tetramethyl-chroman-2-ylmethoxy)-benzylidene]-2,4-thiazolidine-dione}, Δ2-CG {5-[4-(1-methyl-cyclohexylmethoxy)-benzylidene]-thiazolidine-2,4-dione}, Δ2-RG {5-{4-[2-(methyl-pyridin-2-yl-amino)-ethoxy]-benzylidene}-thiazolidine-2,4-dione}, Δ2-PG {5-{4-[2-(5-ethyl-pyridin-2-yl)-ethoxy]-benzylidene}-thiazolidine-2,4-dione} (FIG. 1A), and TG-88 are TZD derivatives with attenuated or unappreciable activity in PPARγ activation, of which the synthesis will be published elsewhere. The identity and purity (≧99%) of these synthetic derivatives were verified by proton nuclear magnetic resonance, high-resolution mass spectrometry, and elemental analysis. For in vitro experiments, these agents at various concentrations were dissolved in DMSO, and were added to cells in medium with a final DMSO concentration of 0.1%. For the in vivo study, TG88 was prepared as a suspension by sonication in a vehicle consisting of 0.5% methylcellulose and polysorbate 80 in sterile water. The pan-caspase inhibitor Z-VAD-FMK was purchased from BD Bioscience. The Cell Death Detection ELISA kit was purchased from Roche Diagnostics (Mannheim, Germany). The Nuclear Extract kit and PPARγ Transcription Factor Assay kit were obtained from Active Motif (Carlsbad, Calif.). Rabbit antibodies against Bcl-xL, Bax, Bak, Bid, and cleaved caspase-9 were purchased from Cell Signaling Technology Inc. (Beverly, Mass.). Rabbit antibodies against Bad, and cytochrome c, and mouse anti-Bcl-2, anti-.-tubulin were from Santa Cruz Biotechnology, Inc. (Santa Cruz, Calif.). Mouse monoclonal anti-actin was from ICN Biomedicals Inc (Costa Mesa, Calif.). Goat anti-rabbit immunoglobulin G (IgG)-horseradish peroxidase conjugates and rabbit anti-mouse IgG horseradish peroxidase conjugates were from Jackson ImmunoResearch Laboratories (West Grove, Pa.). 6C8 Hamster anti-human Bcl-2 antibody for immunoprecipitation was purchased from Pharmingen (San Diego, Calif.).

Cell Culture. LNCaP androgen-dependent ($p53^{+/+}$) and PC-3 androgen-nonresponsive ($P53^{-/-}$) prostate cancer cells were obtained from the American Type Culture Collection (Manassas, Va.), and were maintained in RPMI 1640 medium supplemented with 10% fetal bovine serum (FBS) at 37° C. in a humidified incubator containing 5% $CO_2$. Preparation of the stable Bcl-xL-overexpressing LNCaP clones B11, B1, and B3 were previously described (16).

Cell viability analysis. The effect of individual test agents on cell viability was assessed by using the MTT {[3-(4,5-dimethylthiazol-2-yl)-2,5-diphenyl-2H-tetrazolium bromide]} assay in six to twelve replicates. Cells were seeded and incubated in 96-well, flat-bottomed plates in serum-free media for 24 h, and were exposed to various concentrations of test agents dissolved in DMSO (final concentration, 0.1%) in serum-free RPMI 1640 medium for different time intervals. Controls received DMSO vehicle at a concentration equal to that in drug-treated cells. The medium was removed, replaced by 200 μl of 0.5 mg/ml of MTT in 10% FBS-containing RPMI-1640 medium, and cells were incubated in the $CO_2$ incubator at 37° C. for 2 h. Supernatants were removed from the wells, and the reduced MTT dye was solubilized in 200 μl/well DMSO. Absorbance at 570 nm was determined on a plate reader.

Apoptosis Detection by An Enzyme-Linked Immunosorbent Assay (ELISA). Induction of apoptosis was assessed with a Cell Death Detection ELISA kit (Roche Diagnostics, Mannheim, Germany) by following the manufacturer's instruction. This test is based on the quantitative determination of cytoplasmic histone-associated DNA fragments in the form of mononucleosomes and oligonucleosomes after induced apoptotic death. In brief, $1 \times 10^6$ cells were cultured in a T-25 flask in 10% FBS-containing medium for 24 h, and were treated with the test agents at various concentrations in serum-free medium for 24 h. Both floating and adherent cells were collected, cell lysates equivalent to $5 \times 10^5$ cells were used in the ELISA.

Western Blot Analysis of Cytochrome c Release into the Cytoplasm. Cytosolic-specific, mitochondria-free lysates were prepared according to an established procedure (16). In brief, after individual treatments for 24 h, both the incubation medium and adherent cells in T-75 flasks were collected, and centrifuged at 200×g for 5 min. The pellet fraction was recovered, placed on ice, and triturated with 300 μl of a chilled hypotonic lysis solution [50 mM PIPES-KOH, pH 7.4, containing 220 mM mannitol, 68 mM sucrose, 50 mM KCl, 5 mM EDTA, 2 mM $MgCl_2$, 1 mM DTT, and a mixture of protease inhibitors including 100 μM AEBSF, 80 nM aprotinin, 5 μM bestatin, 1.5 μM E-64 protease inhibitor, 2 μM leupeptin, and 1 μM pepstatin A]. After a 45 min-incubation on ice, the mixture was centrifuged at 200×g for 10 min. The supernatant was collected in a microcentrifuge tube, and centrifuged at 14,000 rpm for 30 min. An equivalent amount of protein (50 μg) from each supernatant was resolved in 10% SDS-polyacrylamide gel. Bands were transferred to nitrocellulose membranes, and analyzed by immunoblotting with anti-cytochrome c antibodies, as described below.

Immunoblotting. Cells in T-75 flasks were collected by scraping, and suspended in 60 μl of phosphate-buffered saline (PBS). Two μl of the suspension was taken for protein analysis using the Bradford assay kit (Bio-Rad, Hercules, Calif.). To the remaining solution was added the same volume of 2×SDS-PAGE sample loading buffer (100 mM Tris-HCl, pH 6.8, 4% SDS, 5% β-mercaptoethanol 20% glycerol, and 0.1% bromophenol blue). The mixture was sonicated briefly, and boiled for 5 min. Equal amounts of proteins were loaded onto 10% SDS-PAGE gels.

After electrophoresis, protein bands were transferred to nitrocellulose membranes in a semidry transfer cell. The transblotted membrane was washed twice with Tris-buffered saline (TBS) containing 0.1% Tween 20 (TBST). After blocking with TBST containing 5% nonfat milk for 40 min, the membrane was incubated with the appropriate primary antibody in TBST-1% nonfat milk at 4° C. overnight. All primary antibodies were diluted 1:1000 in 1% nonfat milk-containing TBST. After treatment with the primary antibody, the membrane was washed three times with TBST for a total of 15 min, followed by incubation with goat anti-rabbit or anti-mouse IgG-horseradish peroxidase conjugates (diluted 1:5000) for 1 h at room temperature and three washes with TBST for a total of 1 h. The immunoblots were visualized by enhanced chemiluminescence.

Analysis of PPARγ activation. The analysis was carried out by using a PPARγ transcription factor ELISA kit (Active Motif, Carlsbad, Calif.), in which an oligonucleotide containing the peroxisome proliferator response element (PPRE) was immobilized onto a 96-well plate. PPARs contained in nuclear extracts bind specifically to this oligonucleotide and are detected through an antibody directed against PPARγ. In brief, PC-3 cells were cultured in RPMI 1640 medium supplemented with 10% FBS, and treated with DMSO vehicle or individual test agents, 10 μM each, for 48 h. Cells were collected, and nuclear extracts were prepared with a Nuclear Extract kit (Active Motif, Carlsbad, Calif.). Nuclear extracts of the same protein concentration from individual treatments were subject to the PPARγ transcription factor ELISA according to the manufacturer's instruction.

Competitive Fluorescence Polarization Assay. The binding affinity of the test agent to Bcl-2 and Bcl-xL was analyzed by a competitive fluorescence polarization assay, in which the ability of the agent to displace the binding of a Bak BH3-domain peptide to either Bcl-2 or Bcl-xL was determined. Flu-BakBH3, a Bak-BH3 peptide labeled at the N-terminus with fluorescein, was purchased from Genemed Synthesis (San Francisco, Calif.). C-Terminal-truncated, His-tagged $Bcl-x_L$ was purchased from EMD Biosciences (San Diego, Calif.), and soluble GST-fused Bcl-2 was obtained from Santa Cruz (Santa Cruz, Calif.). The $K_D$ determination was carried out in a dual-pathlength quartz cell with readings taken at $\lambda_{em}$ 480 nm and $\lambda_{ex}$ 530 nm at room temperature using a luminescence spectrometer according to an established procedure (17).

Determination of $IC_{50}$ values. Data from cell viability and FP assays were analyzed by using the CalcuSyn software (Biosoft, Ferguson, Mo.) to determine $IC_{50}$ values, in which the calculation was based on the medium effect equation (18), i.e., $Log(fa/fu)=m \log(D)-m \log(Dm)$ (equation 1), where fa and fu denote fraction affected and unaffected, respectively; m represents the Hill-type coefficient signifying the sigmoidicity of the dose-effect curve; D and Dm are the dose used and $IC_{50}$, respectively.

Co-immunoprecipitation. PC3 cells treated with 50 μM TG or Δ2-TG for 12 hr were collected, and lysed by NP-40 isotonic lysis buffer with freshly added protease inhibitors (142 mM KCl, 5 mM $MgCl_2$, 10 mM HEPES, pH 7.2, 1 mM EGTA, 0.2% NP-40, 0.2 mM PMSF, and 1 μg/ml, each aprotinin, leupeptin, and pepstatin). After centrifugation at 13000×g for 15 min, the supernatants were collected, preincubated with protein A-Sepharose (Sigma, St. Louis, Mo.) for 15 min, and centrifuged at 1000×g for 5 min. The supernatants were exposed to Bcl-2 or Bcl-xL antibodies in the presence of protein A-Sepharose at 4° C. for 2 h. After brief centrifugation, protein A-Sepharose were collected, washed with the aforementioned lysis buffer 2 times, suspended in 2×SDS sample buffer, and subjected to Western blot analysis with antibodies against Bak.

Xenograft tumor growth. Male NCr athymic nude mice (5-7 weeks of age) were obtained from the National Cancer Institute (Frederick, Md.). The mice were group-housed under conditions of a constant 12-h photoperiod with ad libitum access to sterilized food and water. All experimental procedures utilizing these mice were performed in accordance with protocols approved by the Institutional Laboratory Animal Care and Use Committee of The Ohio State University.

Each mouse was inoculated subcutaneously in the right flank with $5\times10^5$ PC-3 cells suspended in 0.1 ml of serum-free medium containing 30% Matrigel (BD Biosciences, Bedford, Mass.) under isoflurane anesthesia. Forty-eight hours later, mice were randomly divided into three groups (n=8) and were administered daily TG88 at 100 and 200 mg/kg body weight/day by gavage for the duration of the study. Controls received vehicle consisting of 0.5% methylcellulose and 0.1% polysorbate 80 in sterile water. The volume of drug or vehicle administered to each mouse was 0.02 ml/gram body weight. Tumors were measured weekly using calipers and their volumes calculated using a standard formula: $width^2 \times length \times 0.52$. Body weights were measured weekly.

Statistical analysis. For in vitro studies, data were analyzed by one-way ANOVA followed Fisher's LSD for multiple comparisons. These data are expressed as means±SD. For the in vivo study, tumor volume data failed to meet the assumption of noituality (Shapiro-Wilk test) for parametric analysis; thus, group means were compared using the Kruskall-Wallis ANOVA procedure and the Mann-Whitney U test. Tumor growth data are expressed as mean tumor volumes±SE. For all data, differences were considered significant at $P<0.05$. Statistical procedures were performed using SPSS for Windows (SPSS, Inc., Chicago, Ill.).

Results

Development of TZD derivatives lacking PPARγ ligand activity. It was reported that introduction of a double bond adjoining the terminal thiazolidine-2,4-dione ring of RG abrogated its PPARγ ligand property (19). As part of our effort to discern the role of PPARγ activation in the antitumor effects of TZDs, we synthesized this RG derivative and the counterparts of TG, PG, and CG, and examined the ability of the resulting molecules (Δ2-TG, Δ2-RG, Δ2-PG, and Δ2-CG) vis-à-vis their parent TZDs to activate PPARγ in PC-3 cells (FIG. 1).

Among these new compounds, Δ2-RG showed a 77% reduction in the activity in PPARγ activation as compared to RG, which is in line with that reported in the literature (19). In contrast, Δ2-TG, Δ2-PG, and Δ2-CG were completely devoid of the ligand binding activity since the respective levels of PPARγ activation were not statistically different from that of the DMSO vehicle ($P<0.01$). The loss/attenuation of PPARγ activity in these Δ2-derivatives was presumably attributable to the structural rigidity, as a result of the double bond introduction, surrounding the heterocyclic system.

Figure 2:
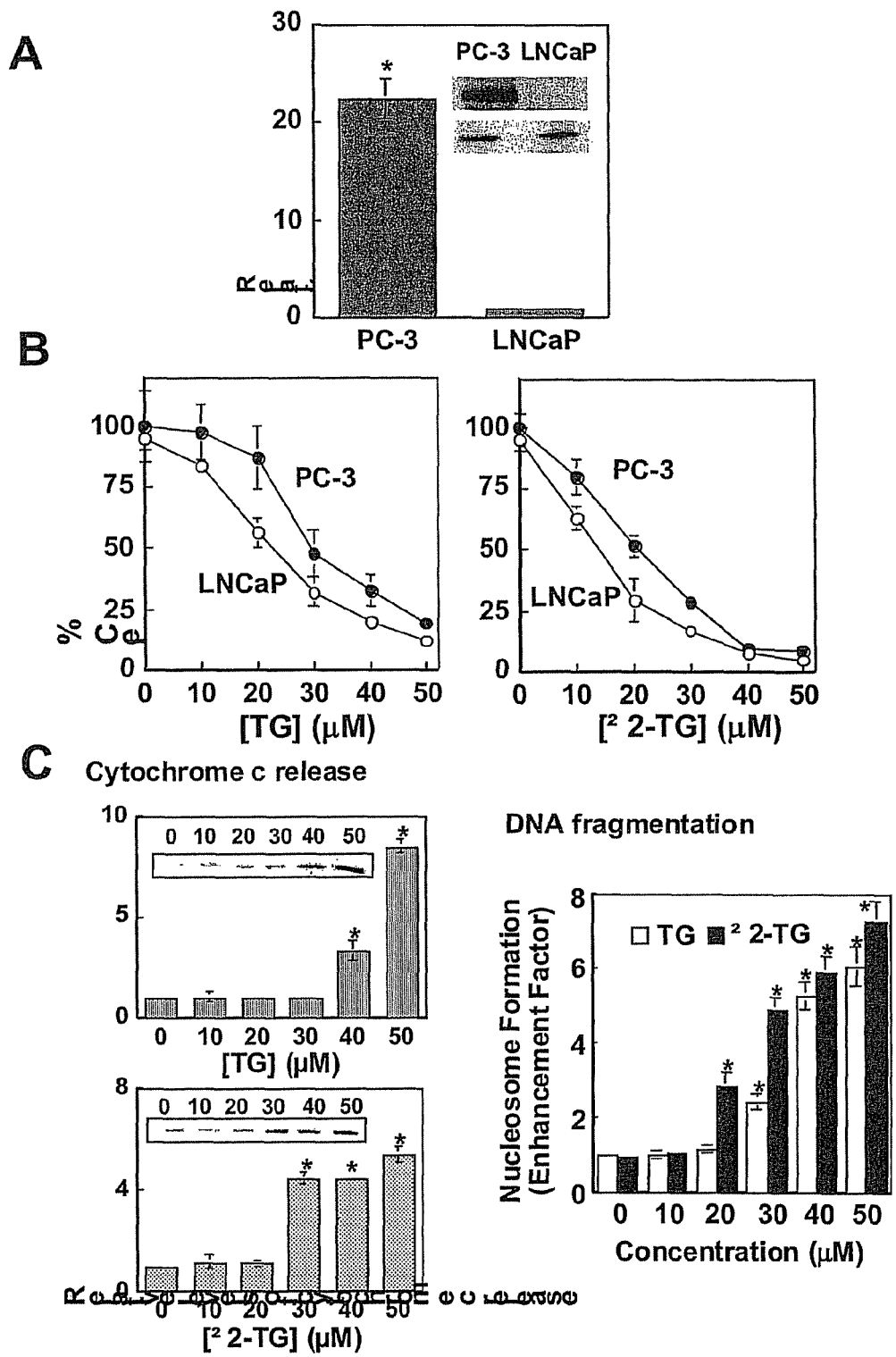
FIG. 2 Evidence that the effect of TG on apoptosis in prostate cancer cells is dissociated from PPARγ activation. (A) Relative PPARγ levels in PC-3 and LNCaP cells, normalized to α-tubulin levels. Each data point represents mean±S.D. (n=3). Inset: Western blot analysis of the expression status of PPARγ (☐☐☐☐☐☐☐☐) and α-tubulin (lower lane) in PC-3 and LNCaP cells. *P<0.01. (B) Dose-dependent effects of TG and Δ2-TG on the cell viability of PC-3 and LNCaP cells. PC-3 cells were exposed to TG or Δ2-TG at the indicated concentrations in serum-free RPMI 1640 medium in 96-well plates for 24 h, and cell viability was assessed by MTT assay. Each data point represents the mean±S.D. (n=6). (C) Evidence of apoptotic death in drug-treated PC-3 cells. Left panel, levels of cytochrome c release into cytoplasm induced by different doses of TG and Δ2-TG. Values are means±S.D. (n=3), normalized to β-actin levels. *P<0.01. PC-3 cells were treated with either agent at the indicated concentration for 24 h in serum-free RMPI 1640 medium for 24 h, and mitochondria-free lysates were prepared. Equivalent amounts of protein from individual lysates were electrophoresed, and probed by Western blotting with anti-cytochrome c antibody (inset; β-actin blots are not shown). Right panel, formation of nucleosomal DNA in PC-3 cells that were treated with TG or Δ2-TG at the indicated concentrations for 24 h. DNA fragmentation was quantitatively measured by a cell death detection ELISA kit. Each data point represents mean±S.D. (n=3).
Figure 3:
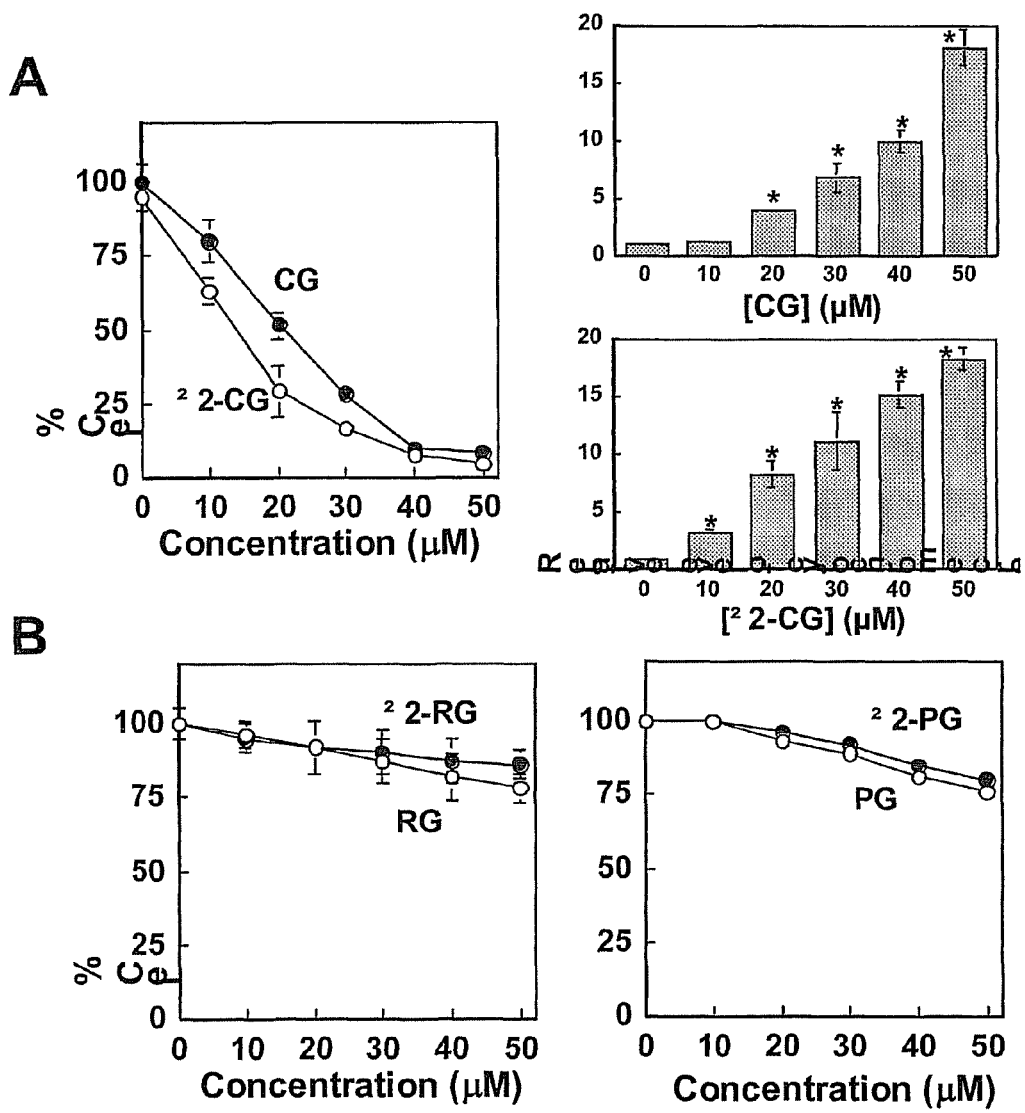
FIG. 3 Differential effects of CG, RG, PG, and their Δ2-derivatives on apoptotic death in PC-3 cells. (A) Dose-dependent effects of CG and Δ2-CG on PC-3 cell viability (left panel) and mitochondrial cytochrome c release (right panel). Values are means±S.D. (n=3). Cytochrome c release levels are normalized β-actin levels. *P<0.01. (B) Dose-dependent effects of RG and Δ2-RG (left panel), and PG and Δ2-PG (right panel) on PC-3 cell viability. PC-3 cells were exposed to individual test agents at the indicated concentrations in serum-free RPMI 1640 medium in 96-well plates for 24 h, and cell viability was assessed by MTT assay. Each data point represents the mean±S.D. (n=6). For the analysis of cytochrome c release, PC-3 cells were treated with the test agent at the indicated concentration for 24 h in serum-free RMPI 1640 medium for 24 h, and mitochondria-free lysates were prepared. Equivalent amounts of protein from individual lysates were electrophoresed, and probed by Western blotting with anti-cytochrome c antibody.

Apoptosis-inducing effects of TZDs on prostate cancer cells are independent of PPARγ activation. We first assessed the dose-dependent growth inhibitory effect of TG and Δ2-TG in two prostate cancer cell lines, androgen-independent PC-3 ($p53^{-/-}$) and androgen-dependent LNCaP ($p53^{+/+}$). Among many genotypic differences, these two cell lines exhibit distinct PPARγ expression status (15), i.e., PPARγ was highly expressed in PC-3 cells, but was deficient in LNCaP cells (FIG. 2A; $P<0.01$). Nevertheless, despite deficiency in PPARγ, LNCaP cells exhibited a higher degree of susceptibility to TG-mediated in vitro antitumor effects as compared to the PPARγ-rich PC-3 cells (FIG. 2B). In addition, Δ2-TG, though devoid of PPARγ-activating activity, was more potent than TG in suppressing cell proliferation in both cell lines. The respective $IC_{50}$ values for TG and Δ2-TG were 30±2 and 20±2 μM in PC-3 cells, and 22±3 and 14±1 μM in LNCaP cells. This growth inhibition was attributable to apoptotic cell death, as evidenced by mitochondrial cytochrome c release and DNA fragmentation in PC-3 cells (FIG. 2C). Similar results were obtained with CG and Δ2-CG with respect to cytochrome c-dependent apoptotic death in PC-3 cells. The relative potency paralleled that of TG and Δ2-TG (FIG. 3A). In contrast, RG, PG, and their Δ2-counterparts showed marginal effects, even at 50 μM, on apoptotic death in PC-3 cells (FIG. 3B). Together, these data suggest that TZDs mediated apoptosis induction in prostate cancer cell systems irrespective of PPARγ activation.

Apoptosis-active TZDs are inhibitors of Bcl-xL and Bcl-2 functions. Our mechanistic study indicated that TG and Δ2-TG were able to sensitize PC-3 cells to the apoptosis-inducing effect of the phosphoinositide 3-kinase (PI3K) inhibitor LY294002 (unpublished data). This finding, together with our recent report that attributed the resistance of PC-3 cells to LY294002-induced apoptosis to Bcl-xL overexpression (16), suggests a plausible link between TZD-induced apoptosis and modulation of the functions of Bcl-xL and/or other Bcl-2 members.

Accordingly, we examined this putative link by two distinct approaches at both transcriptional and post-translational levels. First, we assessed the time-dependent effect of TG (30 μM) on the expression of different Bcl-2 family members in PC-3 cells, including Bcl-xL, Bcl-2, Bax, Bak, Bad, and Bid. This analysis was based on recent reports that treatment of MCF-7 breast cancer and HepG2 hepatoma cells with high doses of TG altered the expression levels of certain Bcl-2 members (9, 14). Second, in light of the recent discovery of small-molecule Bcl-2 or Bcl-xL inhibitors that disrupt BH3 domain-mediated interactions with proapoptotic Bcl-2 members (20-26), we investigated the in vitro effects of TZDs and their Δ2-counterparts on the antiapoptotic function of Bcl-xL and Bcl-2. It is well understood that the ability of Bcl-xL and Bcl-2 to form heterodimers with proapoptotic Bcl-2 members via BH3-domain binding plays a key role in their antiapoptotic functions. Therefore, a well-established competitive fluorescence polarization (FP) analysis was used to examine the effects of TZDs on the binding of a Bak BH3-domain peptide to Bcl-xL and Bcl-2.

Figure 4:
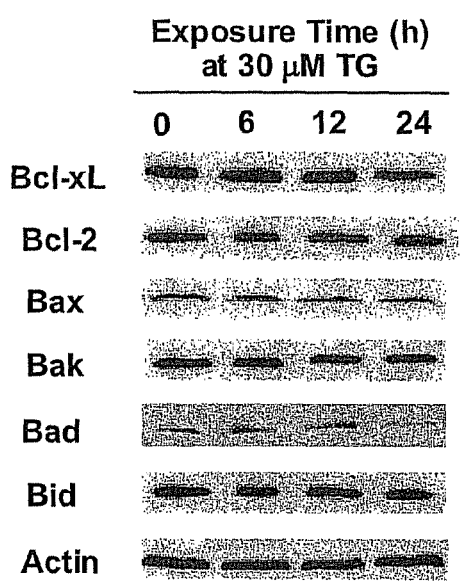
FIG. 4 Effect of TG on the expression levels of Bcl-2 family members in PC-3 cells. PC-3 cells were exposed to 30 μM TG in serum-free RPMI 1640 medium for the indicated times. Equivalent amounts of protein from cell lysates were electrophoresed, and probed by Western blotting with individual antibodies (left panel). The bar graph depicts the relative expression levels, normalized to actin levels, at the indicated time after drug treatment.
Figure 4:
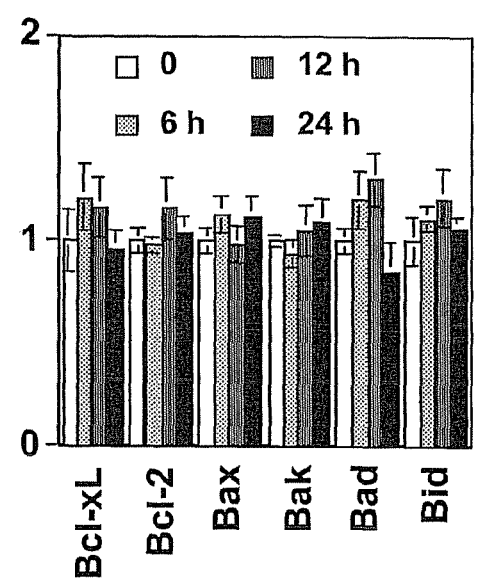

FIG. 4 indicates that with the exception of a slight decrease in Bad expression at 24 h, the exposure of PC-3 cells to 30 μM TG did not cause appreciable change in the expression level of any of these Bcl-2 members throughout the course of investigation.

Figure 5:
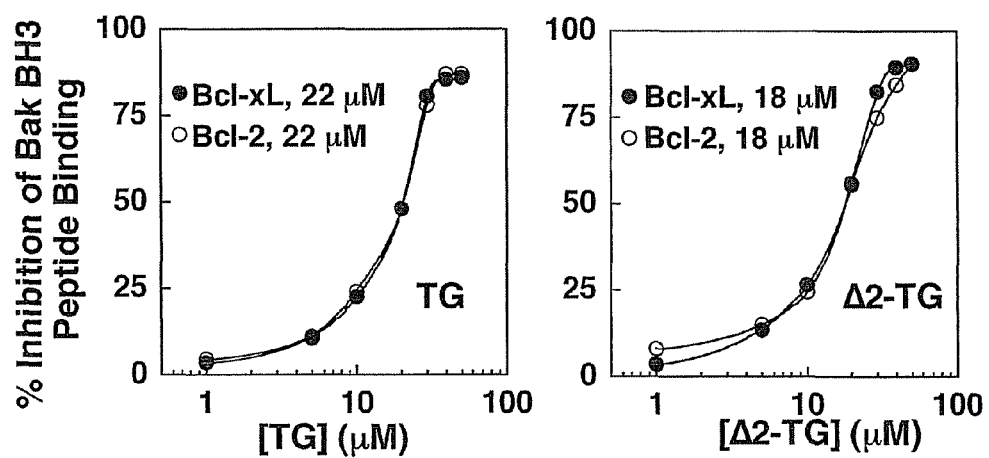
FIG. 5 Differential inhibition of BH3 domain-mediated protein interactions of Bak BH3 peptide with Bcl-xL or Bcl-2 by TZDs and their Δ2-derivatives. (A) Displacement of Flu-BakBH3 peptide from Bcl-xL or Bcl-2 by TG (left panel) and Δ2-TG (right panel). (B) $IC_{50}$ values of individual TZDs and Δ2-TZDs for inhibiting the BH3-mediated protein interactions.

Nevertheless, data from the competitive FP analysis suggest that TG, CG, and their Δ2-counterparts inhibited the antiapoptotic functions of Bcl-xL and Bcl-2 by disrupting the BH3 domain-mediated interactions with proapoptotic Bcl-2 members. FIG. 5A depicts the ability of TG and Δ2-TG to displace the binding of a fluorescein-labeled Bak BH3 domain peptide to Bcl-xL and Bcl-2. It is noteworthy that both compounds inhibited the BH3 peptide binding to Bcl-xL and Bcl-2 with equal potency, a distinct difference from many reported small-molecule inhibitors that showed discriminative affinity between these two antiapoptotic Bcl-2 members. The $IC_{50}$ values for the inhibition of Bak BH3 peptide binding to either Bcl-xL or Bcl-2 were 22±1 and 18±1 μM, for TG and Δ2-TG, respectively (FIG. 5A). CG and Δ2-CG showed similar effects on the protein-protein interactions with comparable $IC_{50}$ values (FIG. 5B). On the other hand, RG, Δ2-RG, PG, and Δ2-PG, which were ineffective in inducing apoptotic death even at high doses, showed poor inhibitory activities with $IC_{50}$ significantly greater than 50

In light of the integral role of Bcl-2 members in the modulation of mitochondrial integrity, these in vitro binding data suggest that interference of the ability of Bcl-2 and Bcl-xL to bind with their proapoptotic Bcl-2 partners represented a major pathway for TG, Δ2-TG, and CG counterparts to exert their apoptotic action. To corroborate this premise, we obtained two lines of evidence, 1) TG and Δ2-TG attenuated the binding of intracellular Bcl-2 and Bcl-xL to proapoptotic Bcl-2 members, and 2) overexpression of Bcl-xL provided protection against the drug-induced apoptosis.

Figure 6:
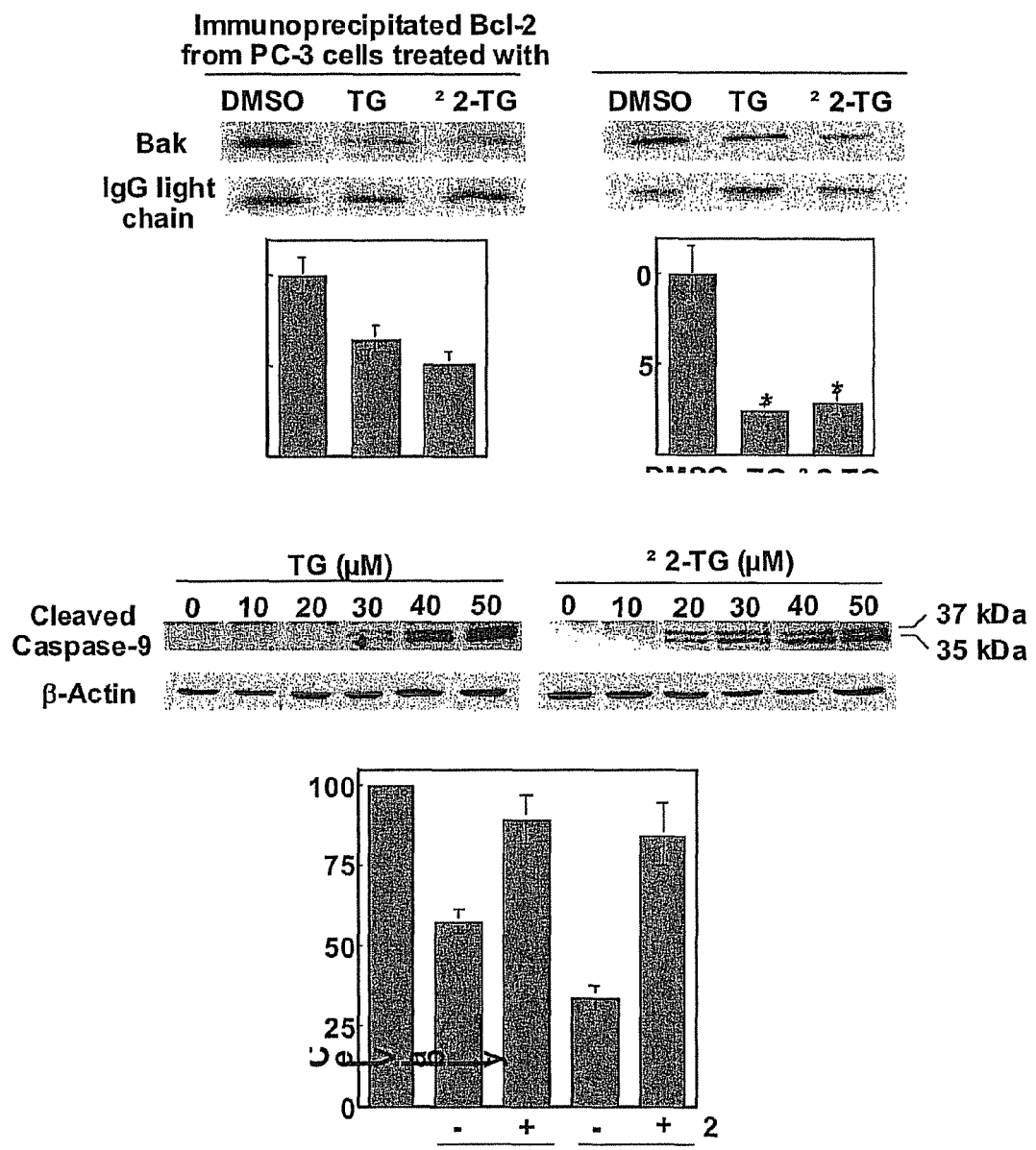
FIG. 6 TG and Δ2-TG trigger caspase-dependent apoptotic death by inhibiting heterodimer formation of Bcl-2 and Bcl-xL with Bak. (A) Effect of TG and Δ2-TO on the dynamics of Bcl-2/Bak (left panel) and Bcl-xL/Bak (right panel) interactions in PC-3 cells. PC-3 cells were treated; with 50 μM TG or Δ2-TG for 12 h, and cell lysates were immunoprecipitated with anti-Bcl-2 or anti-Bcl-xL antibodies. The immunoprecipitates were probed with anti-Bak antibodies by Western blot analysis (WB) as described in the Materials and Methods. The bar graphs indicate the relative Bak levels, normalized to IgG light chains levels, in the three treatments. Values are means±S.D. (n=3). *P<0.01. (B) Dose-dependent effect of TG and Δ2-TG on caspase-9 activation in PC-3 cells. PC-3 cells were treated with TG or Δ2-TG at the indicated concentrations for 24 h. Caspase-9 antibodies recognize the large subunits (35 and 37 kDa). (C) Protection of TG and Δ2-TG-induced apoptosis in PC-3 cells by the pan-caspase inhibitor Z-VAD-FMK. PC-3 cells were pretreated with 100 μM Z-VAD-FMK 30 minute before exposure to 30 μM TG or Δ2-TG in serum-free RPMI 1640 medium in 96-well plates for 24 h, and cell viability was assessed by MTT assay. Each data point represents the mean±S.D. (n=6). *P<0.01.

Effect of TG and Δ2-TG on intracellular Bcl-2 and Bcl-xL binding to Bak. The functional relationship among different types of Bcl-2 family members in regulating the apoptosis machinery has been the focus of many recent investigations (27). One school of thought is that Bcl-2 and Bcl-xL sequester Bax, Bak and other proapoptotic Bcl-2 members through BH3 domain-mediated heterodimerization, thereby abrogating their proapoptotic effects (28-32). For example, electrophoretic introduction of Bak or Bax BH3-domain peptides into PC-3 cells disrupted Bcl-2-Bak heterodimer formation, which resulted in the liberation of Bax and Bak to mediate apoptotic death via a caspase-dependent pathway (32). Consequently, to validate the mode of action of TG and Δ2-TG, we assessed the effects on the dynamics of Bcl-2/Bak and Bcl-xL/Bak interactions in PC-3 cells. Lysates from PC-3 cells treated with TG or Δ2-TG (50 μM) vis-à-vis DMSO for 12 h were immunoprecipitated with antibodies against Bcl-2 or Bcl-xL. Probing of the immunoprecipitates with anti-Bak antibodies by Western blotting indicates that the level of Bak associated with Bcl-2 and Bcl-xL was significantly reduced as compared to the DMSO control (FIG. 6A; P<0.01). This decrease in intracellular associations bore out the in vitro binding data that TG and Δ2-TG inhibited the interactions of Bcl-xL and Bcl-2 with the Bak BH3-domain peptide. We further demonstrated that treatment of PC-3 cells with TG or Δ2-TG led to caspase-9 activation in a dose-dependent manner (FIG. 6B) similar to that of cytochrome c release (FIG. 2A). Furthermore, pretreatment of PC-3 cells with the pan-caspase inhibitor Z-VAD-FMK protected cells from TG- and Δ2-TG-induced apoptosis (FIG. 6C; P<0.01), confirming the involvement of caspase activation in apoptotic death.

Figure 7:
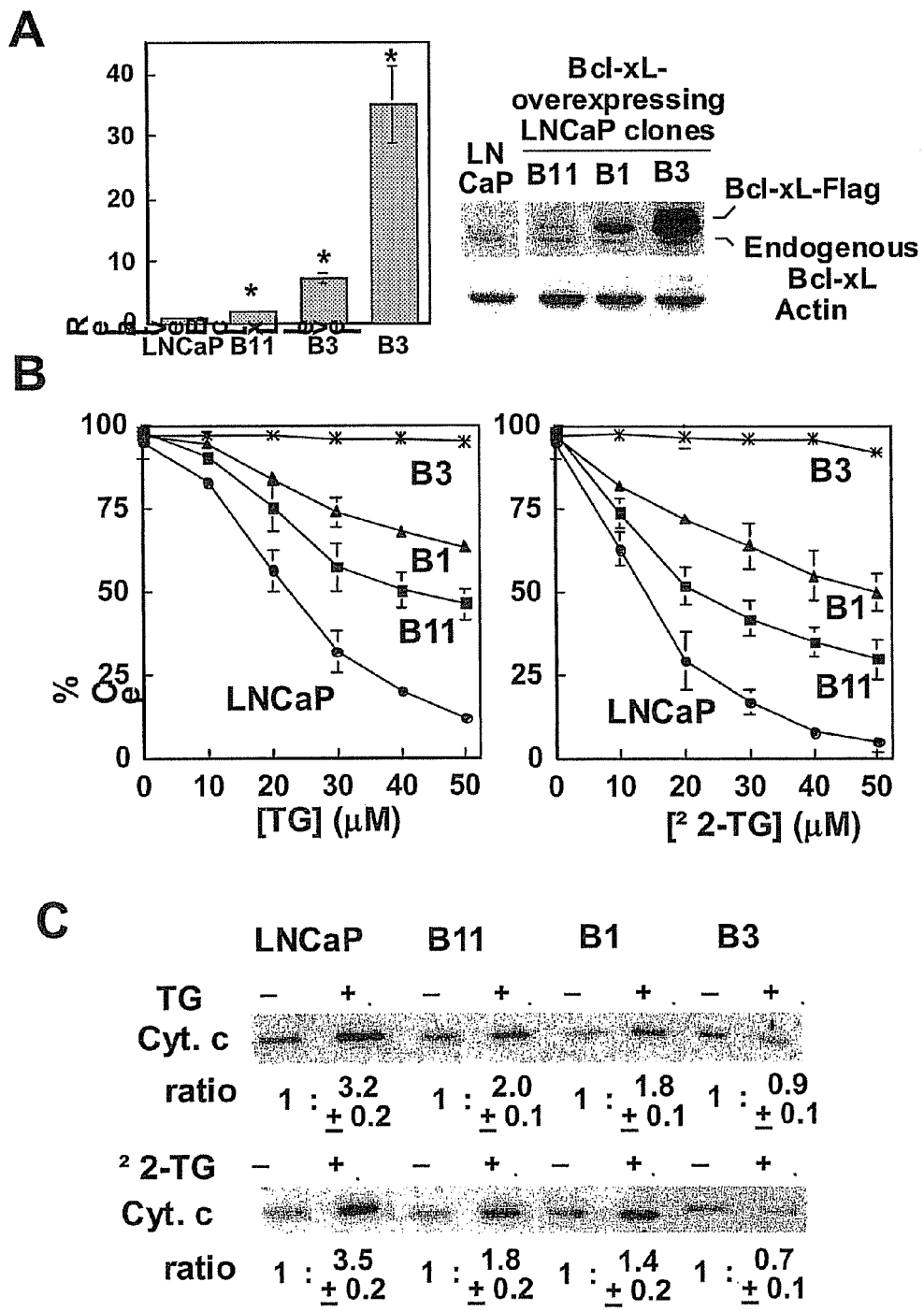
FIG. 7 Ectopic Bcl-xL protects LNCaP cells from TG- and Δ2-TG-induced apoptosis by attenuating cytochrome c release in an expression level-dependent manner. (A) Left panel, ascending expression levels of ectopic Bcl-xL in B11, B1, and B3 clones. Values are means±S.D. (n=3). *P<0.01. Right panel, Western blot analysis. The band for ectopic Bcl-xL contained a FLAG tag (8 amino acids long) from the construct, thus migrating slower than endogenous Bcl-xL. (B) Dose-dependent effects of TG (left panel) and Δ2-TG (right panel) on apoptosis in LNCaP, B11, B1, and B3 cells. Data are mean±S.D. (n=3). (C) Ectopic expression of Bcl-xL inhibits the effect of TG (50 μM) and Δ2-TG (50 μM) on cytochrome c release. Cells were treated with DMSO vehicle (−) or with 50 μM TG or Δ2-TG. Cytosol-specific, mitochondria-free lysates were prepared. Equivalent amounts of protein from individual lysates were electrophoresed, and probed by Western blotting with anti-cytochrome c antibody. The relative ratios of cytoplasmic cytochrome c in drug-treated to vehicle-treated cells are shown below the Western blots. Values are means±S.D. (n=3).

Bcl-xL overexpression protects prostate cancer cells from TG- and Δ2-TG-Induced Apoptosis. We previously reported that LNCaP cells exhibited lower Bcl-xL expression levels as compared to PC-3 cells (16), which underscored differences between these two cell lines in the susceptibility to the apoptotic effects of TG, CG, and their Δ2-counterparts. To confirm that the inhibition of Bcl-xL functions plays a key role in the apoptosis induction, we examined the impact of Bcl-xL overexpression on the susceptibility to TG- and Δ2-TG-induced cell death in LNCaP cells. Three transfected clones (B11, B1, and B3) that displayed ascending expression levels of Bcl-xL were tested vis-à-vis parental LNCaP cells (FIG. 7A). FIG. 7B depicts the differential protective effects of ectopic Bcl-xL on TG- and Δ2-TG-induced apoptotic death among the three Bcl-xL clones, in which the extent of cytoprotection correlated with the Bcl-xL expression levels. Overexpression of ectopic Bcl-xL conferred partial protection to the cytotoxic effects of TG and Δ2-TG in B11 and B1 cells (P<0.01), whereas the excessive expression in B3 cells completely overcame the inhibitory effect of TG and Δ2-TG on Bcl-xL functions (P<0.01). This protective effect was correlated with the inhibition of TG- and Δ2-TG-induced cytochrome c release (FIG. 7C; P<0.01).

Figure 8:
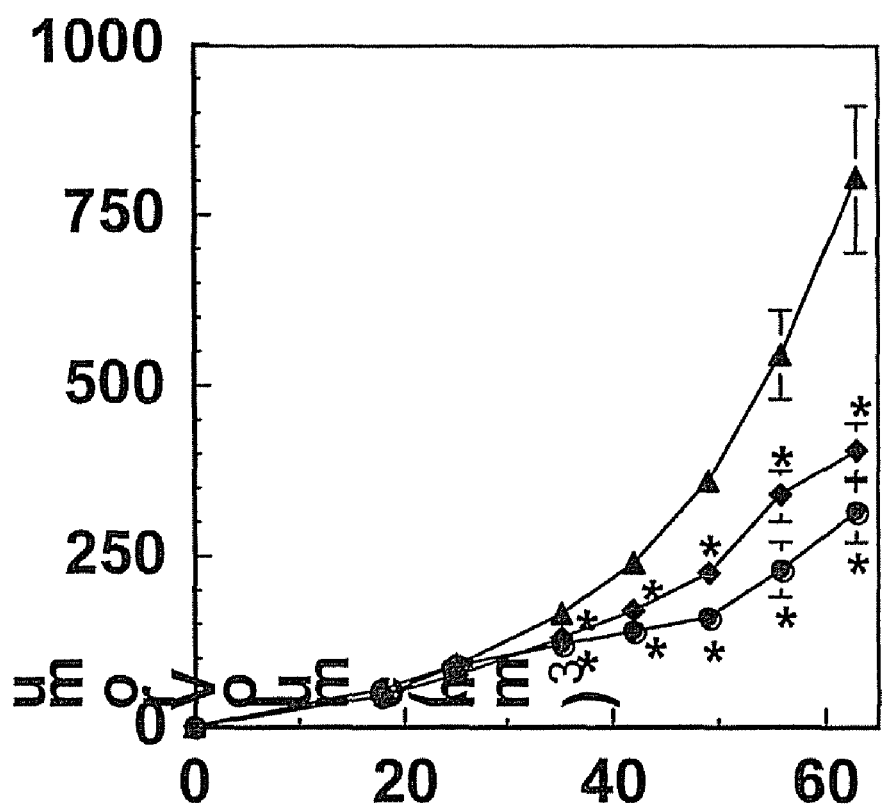
FIG. 8 Effect of oral TG-88 at 100 and 200 mg/kg on the growth of PC-3 tumors in nude mice. Each mouse was inoculated subcutaneously in the right flank with $5 \times 10^5$ PC-3 cells suspended in 0.1 ml of serum-free medium containing 30% Matrigel under isoflurane anesthesia. Forty-eight hours later, mice were randomly divided into three groups (n=8) and were administered daily TG88 at 100 and 200 mg/kg body weight/day by gavage for the duration of the study. Controls received vehicle consisting of 0.5% methylcellulose and 0.1% polysorbate 80 in sterile water. Values are means±SE (n=8). *P<0.05 as compared to the control group.

Development of potent Δ2-TG-derived Bcl-xL/Bcl-2 binding inhibitors. TG has previously been demonstrated to be effective in suppressing PC-3 xenograft tumor growth at 500 g/kg/day (33). Dissociation of the effect of TG on apoptosis from PPARγ activation provided a molecular rationale to structurally optimize Δ2-TG to develop potent Bcl-xL/Bcl-2 binding inhibitors. Accordingly, we synthesized a series of Δ2-TG derivatives, and their activities in inhibiting BH3 domain-mediated Bcl-xL-Bak peptide binding were examined (Chen, manuscript in preparation). Among more than 30 derivatives examined, TG-88 represented an optimal agent with an-order-of-magnitude higher potency than Δ2-TG in FP-based Bcl-xL binding inhibition ($IC_{50}$, 1.8±0.2 μM) and PC-3 cell proliferation ($IC_{50}$, 2.5±0.2 μM). In addition, like Δ2-TG, TG-88 lacked appreciable activity in PPARγ activation. To examine its therapeutic relevance, we assessed the in vivo effect of daily oral TG-88 at two different doses, 100 and 200 mg/kg, on the growth of PC-3 xenograft tumors (FIG. 8). All animals tolerated the treatments well without observable signs of toxicity and were characterized by stable body weights throughout the course of study. No gross pathological abnormalities were noted at necropsy after 63 days of treatment. As shown, both treatments displayed a significant inhibitory effect (P<0.05) when the tumors of control animals entered an exponential growth phase at day 35 and beyond. After 63 days of treatment, the extents of tumor growth inhibition were 50% and 61% for groups receiving 100 and 200 mg/kg/day, respectively.

Although accumulating evidence suggests that TG and CG mediate PPARγ-independent antitumor effects, the underlying mechanism remains undefined. Here, we obtained several lines of evidence that the effects of these TZDs on apoptosis in prostate cancer cells were attributable, in part, to the inhibition of Bcl-xL/Bcl-2 functions independently of PPARγ activation. First, Δ2-TG and Δ2-CG, though devoid of PPARγ activity, exhibited slightly higher potency than TG and CG, respectively, in inducing apoptotic death irrespective of differences in PPARγ expression levels between LNCaP and PC-3 cells. In contrast, RG and PG, two TZDs currently in clinical use for the treatment of diabetes, lacked appreciable effects on apoptosis despite their higher potency in PPARγ activation than TG and CG. Second, a correlation exists between the potency in inhibiting BH3 peptide binding to Bcl-xL or Bcl-2 and the effectiveness in inducing apoptosis in prostate cancer cells. For example, the inability of RG and PG to trigger apoptotic death was reflected in their weak potency in displacing BH3 domain-mediated interactions. It is interesting that introduction of a double bond adjoining the terminal thiazolidine-2,4-dione ring in TG and CG enhanced the Bcl-xL/Bcl-2 inhibitory activity, while abrogating the ability to activate PPARγ. Presumably, this change in pharmacological profiles was attributable to the structural rigidity surrounding the heterocyclic system as a result of the double bond introduction. Third, the immunoprecipitation study indicates that the level of Bak associated with Bcl-2 and Bcl-xL was greatly reduced in TG- and Δ2-TG-treated cells as compared to DMSO control. Disruption of the BH3 domain-mediated interactions-led to the liberation of proapoptotic Bcl-2 members, which caused cells to undergo apoptosis by facilitating cytochrome c release and caspase-9 activation. This premise was borne out by the ability of Z-VAD-FMK to protect cells from TG- and Δ2-TG-induced apoptosis. Fourth, overexpression of Bcl-xL provided LNCaP cells protection against TG- and Δ2-TG-induced apoptosis.

Considering the pivotal role of Bcl-xL and Bcl-2 in regulating mitochondrial integrity, this new mode of action provides a molecular framework to account for the PPARγ-independent effects of TZDs on apoptotic death in cancer cells. It is also noteworthy that TG, CG, and their Δ2-derivatives lack specificity in recognizing Bcl-xL and Bcl-2. This relaxed specificity might prove advantageous in light of the importance of both Bcl-2 members in regulating apoptosis thresholds to chemotherapeutic agents.

In summary, the impetus of the dissociation of the in vitro antitumor activities of TZDs from PPARγ activation is multifold. First, although TG has been shown to reduce the growth of xenograft tumors in nude mice (33), this PPARγ agonist has also been reported to promote the development of colon tumors and enhance colon polyp formation in APC$^{Min}$ mice that are genetically predisposed to intestinal neoplasia (35, 36). Thus, a crucial issue that warrants investigation is the role of PPARγ activation in tumorigenic promotion vis-à-vis antitumor effects in these animal model studies. Conceivably, TZDs and their PPARγ-inactive derivatives provide useful tools to shed light onto the link between PPARγ activation and increased cancer risk. Second, from a translational perspective, separation of these two pharmacological activities provides molecular underpinnings to use TZDs, especially Δ2-TG and Δ2-CG, as molecular platforms to design Bcl-xL/Bcl-2 inhibitors with greater in vitro and in vivo antitumor potency. Third, due to the heterogeneous nature of prostate cancer, different prostate tumor cell lines display differential sensitivity to various apoptotic signals. For example, PC-3 cells are able to resist apoptotic signals emanating from withdrawal of trophic factors, and exposure to cytokines and chemotherapeutic agents, in part, due to elevated levels of Akt activation and Bcl-xL overexpression. Consequently, these molecules have translational relevance to be developed into antitumor agents for the prevention and/or therapy of cancers alone or in combination with other treatments. The proof of principle for this premise was TG-88, a close structural analogue of Δ2-TG, with an order-of-magnitude higher potency than Δ2-TG in blocking Bcl-xL binding and inhibiting PC-3 cell proliferation. Oral TG-88 at 100 and 200 mg/kg/day was effective in suppressing PC-3 xenograft tumor growth without causing weight loss or apparent toxicity, indicating its oral bioavailability and potential clinical use. Further development of these novel agents for the prevention and/or treatment of prostate cancer is currently underway.

The examples herein are for illustrative purposes only and are not meant to limit the scope of the invention.

REFERENCES

1. Day, C. Thiazolidinediones: a new class of antidiabetic drugs. Diabet Med, 16: 179-192, 1999.
2. Koeffler, H. P. Peroxisome proliferator-activated receptor gamma and cancers. Clin Cancer Res, 9: 1-9, 2003.
3. Tontonoz, P., Singer, S., Forman, B. M., Sarraf, P., Fletcher, J. A., Fletcher, C. D., Brun, R. P., Mueller, E., Aitiok, S., Oppenheim, H., Evans, R. M., and Spiegelman, B. M. Terminal differentiation of human liposarcoma cells induced by ligands for peroxisome proliferator-activated receptor gamma and the retinoid X receptor. Proc Natl Acad Sci USA, 94: 237-241, 1997.
4. Gupta, R. A., Brockman, J. A., Sarraf, P., Willson, T. M., and DuBois, R. N. Target genes of peroxisome proliferator-activated receptor gamma in colorectal cancer cells. J Biol Chem, 276: 29681-29687, 2001.
5. Altiok, S., Xu, M., and Spiegelman, B. M. PPARgamma induces cell cycle withdrawal: inhibition of E2F/DP DNA-binding activity via down-regulation of PP2A. Genes Dev, 11: 1987-1998, 1997.
6. Palakurthi, S. S., Aktas, H., Grubissich, L. M., Mortensen, R. M., and Halperin, J. A. Anticancer effects of thiazolidinediones are independent of peroxisome proliferator-activated receptor gamma and mediated by inhibition of translation initiation. Cancer Res, 61: 6213-6218, 2001.
7. Takeda, K., Ichiki, T., Tokunou, T., Iino, N., and Takeshita, A. 15-Deoxy-delta 12,14-prostaglandin J2 and thiazolidinediones activate the MEK/ERK pathway through phosphatidylinositol 3-kinase in vascular smooth muscle cells. J Biol Chem, 276: 48950-48955, 2001.
8. Gourii-Berthold, I., Berthold, H. K., Weber, A. A., Ko, Y., Seul, C., Vetter, H., and Sachinidis, A. Troglitazone and rosiglitazone induce apoptosis of vascular smooth muscle cells through an extracellular signal-regulated kinase-independent pathway. Naunyn Schmiedebergs Arch Pharmacol, 363: 215-221, 2001.
9. Bae, M. A. and Song, B. J. Critical role of c-Jun N-terminal protein kinase activation in troglitazone-induced apoptosis of human HepG2 hepatoma cells. Mol Pharmacol, 63: 401-408, 2003.
10. Baek, S. J., Wilson, L. C., Hsi, L. C., and Eling, T. E. Troglitazone, a peroxisome proliferator-activated receptor gamma (PPAR gamma) ligand, selectively induces the early growth response-1 gene independently of PPAR gamma. A novel mechanism for its anti-tumorigenic activity. J Biol Chem., 278: 5845-5853, 2003.
11. Motomura, W., Okumura, T., Takahashi, N., Obara, T., and Kohgo, Y. Activation of peroxisome proliferator-activated receptor gamma by troglitazone inhibits cell growth through the increase of p27KiP1 in human. Pancreatic carcinoma cells. Cancer Res, 60: 5558-5564, 2000.
12. Sugimura, A., Kiriyama, Y., Nochi, H., Tsuchiya, H., Tamoto, K., Sakurada, Y., Ui, M., and Tokumitsu, Y. Troglitazone suppresses cell growth of myeloid leukemia cell lines by induction of p21WAF1/CIP1 cyclin-dependent kinase inhibitor. Biochem Biophys Res Commun, 261: 833-837, 1999.
13. Okura, T., Nakamura, M., Takata, Y., Watanabe, S., Kitami, Y., and Hiwada, K. Troglitazone induces apoptosis via the p53 and Gadd45 pathway in vascular smooth muscle cells. Eur J Pharmacol, 407: 227-235, 2000.
14. Elstner, E., Muller, C., Koshizuka, K., Williamson, E. A., Park, D., Asou, H., Shintaku, P., Said, J. W., Heber, D., and 14. Koeffler, H. P. Ligands for peroxisome proliferator-activated receptorgamma and retinoic acid receptor inhibit growth and induce apoptosis of human breast cancer cells in vitro and in BNX mice. Proc Natl Acad Sci USA, 95: 8806-8811, 1998.
15. Mueller, E., Smith, M., Sarraf, P., Kroll, T., Aiyer, A., Kaufman, D. S., Oh, W., Demetri, G., Figg, W. D., Zhou, X. P., Eng, C., Spiegelman, B. M., and Kantoff, P. W. Effects of ligand activation of peroxisome proliferator-activated receptor gamma in human prostate cancer. Proc Natl Acad Sci USA, 97: 10990-10995, 2000.
16. Yang, C. C., Lin, H. P., Chen, C. S., Yang, Y. T., Tseng, P. H., and Rangnekar, V. M. Bcl-xL mediates a survival mechanism independent of the phosphoinositide 3-kinase/Akt pathway in prostate cancer cells. J Biol Chem, 278: 25872-25878, 2003.
17. Dandliker, W. B., Hsu, M. L., Levin, J., and Rao, B. R. Equilibrium and kinetic inhibition assays based upon fluorescence polarization. Methods Enzymol, 74 Pt C: 3-28, 1981.
18. Chou, T. C. and Talalay, P. Quantitative analysis of dose-effect relationships: the combined effects of multiple drugs or enzyme inhibitors. Adv Enzyme Regul, 22: 27-55, 1984.
19. Forman, B. M., Tontonoz, P., Chen, J., Brun, R. P., Spiegelman, B. M., and Evans, R. M. 15-Deoxy-delta 12, 14-prostaglandin 32 is a ligand for the adipocyte determination factor PPAR gamma. Cell, 83: 803-812, 1995.
20. Wang, J. L., Liu, D., Zhang, Z. J., Shan, S., Han, X., Srinivasula, S. M., Croce, C. M., Alnemri, E. S., and Huang, Z. Structure-based discovery of an organic compound that binds Bcl-2 protein and induces apoptosis of tumor cells. Proc Natl Acad Sci USA, 97: 7124-7129, 2000.
21. Degterev, A., Lugovskoy, A., Cardone, M., Mulley, B., Wagner, G., Mitchison, T., and Yuan, 3. Identification of small-molecule inhibitors of interaction between the BH3 domain and Bcl-xL. Nat Cell Biol, 3: 173-182, 2001.
22. Tzung, S. P., Kim, K. M., Basanez, G., Giedt, C. D., Simon, J., Zimmerberg, J., Zhang, K. Y., and Hockenbery, D. M. Antimycin A mimics a cell-death-inducing Bcl-2 homology domain 3. Nat Cell Biol, 3: 183-191, 2001.
23. Enyedy, I. J., Ling, Y., Nacro, K., Tomita, Y., Wu, X., Cao, Y., Guo, R., Li, B., Zhu, X. Huang, Y., Long, Y. Q., Roller, P. P., Yang, D., and Wang, S. Discovery of small-molecule inhibitors of Bcl-2 through structure-based computer screening. J Med Chem, 44: 4313-4324, 2001.
24. Lugovskoy, A. A., Degterev, A. I., Fahmy, A. F., Zhou, P., Gross, J. D., Yuan, J., and Wagner, G. A novel approach for characterizing protein ligand complexes: molecular basis for specificity of small-molecule Bcl-2 inhibitors. J Am Chem Soc, 124: 1234-1240, 2002.
25. Chan, S. L., Lee, M. C., Tan, K. O., Yang, L. K., Lee, A. S., Flotow, H., Fu, N.Y., Butler, M. S., Soejarto, D. D., Buss, A. D., and Yu, V. C. Identification of chelerythrine as an inhibitor of BclXL function. J Biol Chem, 278: 20453-20456, 2003.
26. Zhang, M., Liu, H., Guo, R., Ling, Y., Wu, X., Li, B., Roller, P. P., Wang, S., and Yang, D. Molecular mechanism of gossypol-induced cell growth inhibition and cell death of HT-29 human colon carcinoma cells. Biochem Pharmacol, 66: 93-103, 2003.
27. Cory, S., Huang, D. C., and Adams, J. M. The Bcl-2 family: roles in cell survival and oncogenesis. Oncogene, 22: 8590-8607, 2003.
28. Sattler, M., Liang, H., Nettesheim, D., Meadows, R. P., Harlan, J. E., Eberstadt, M., Yoon, H. S., Shuker, S. B., Chang, B. S., Minn, A. J., Thompson, C. B., and Fesik, S. W. Structure of Bcl-xL-Bak peptide complex: recognition between regulators of apoptosis. Science, 275: 983-986, 1997.
29. Diaz, J. L., Oltersdorf, T., Home, W., McConnell, M., Wilson, G., Weeks, S., Garcia, T., and Fritz, L. C. A common binding site mediates heterodimerization and homodimerization of Bcl-2 family members. J Biol Chem, 272: 11350-11355, 1997.
30. Otter, I., Conus, S., Ravn, U., Rager, M., Olivier, R., Monney, L., Fabbro, D., and Borner, C. The binding properties and biological activities of Bcl-2 and Bax in cells exposed to apoptotic stimuli. J Biol Chem, 273: 6110-6120, 1998.
31. Nouraini, S., Six, E., Matsuyama, S., Krajewski, S., and Reed, J. C. The putative pore-forming domain of Bax regulates mitochondrial localization and interaction with Bcl-X(L). Mol Cell Biol, 20: 1604-1615, 2000.
32. Finnegan, N. M., Curtin, J. F., Prevost, G., Morgan, B., and Cotter, T. G. Induction of apoptosis in prostate carcinoma cells by BH3 peptides which inhibit Bak/Bcl-2 interactions. Br J Cancer, 85: 115-121, 2001.
33. Kubota, T., Koshizuka, K., Williamson, E. A., Asou, H., Said, J. W., Holden, S., Miyoshi, I., and Koeffler, H. P. Ligand for peroxisome proliferator-activated receptor gamma (troglitazone) has potent antitumor effect against human prostate cancer both in vitro and in vivo. Cancer Res, 58: 3344-3352, 1998.
34. Sarraf, P., Mueller, E., Jones, D., King, F. J., DeAngelo, D. J., Partridge, J. B., Holden, S. A., Chen, L. B., Singer, S., Fletcher, C., and Spiegelman, B. M. Differentiation and reversal of malignant changes in colon cancer through PPARgamma. Nat Med, 4: 1046-1052, 1998.
35. Lefebvre, A. M., Chen, I., Desreumaux, P., Najib, J., Fruchart, J. C., Geboes, K., Briggs, M., Heyman, R., and Auwerx, J. Activation of the peroxisome proliferator-activated receptor gamma promotes the development of colon tumors in C57BL/6J-APCMin/+ mice. Nat Med, 4: 1053-1057, 1998.
36. Saez, E., Tontonoz, P., Nelson, M. C., Alvarez, J. G., Ming, U. T., Baird, S. M., Thomazy, V. A., and Evans, R. M. Activators of the nuclear receptor PPARgamma enhance colon polyp formation. Nat Med, 4: 1058-1061, 1998.

The invention claimed is:

1. A method of treating prostate cancer, the method comprising administering to a subject in need thereof a therapeutically effective amount of a compound of formula III

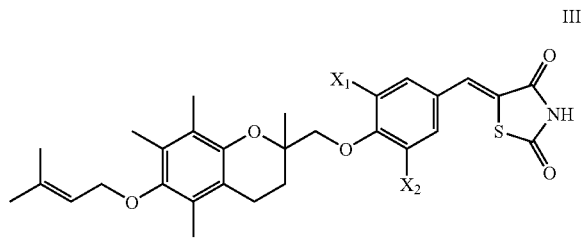

wherein $X_1$ is H, alkyl, alkoxy, halo, nitro, haloalkylaryl, haloaryl, alkylaryl, and combinations thereof; and
$X_2$ is alkyl other than methyl, alkoxy other than methyl, halo other than bromo, and combinations thereof;
and pharmaceutically acceptable salts thereof.

2. The method according to claim 1, wherein the compound is administered orally, intravenously, intramuscularly, subcutaneously, or intraperitoneally.

3. The method according to claim 2, wherein the therapeutically effective amount administered is in the range of about 0.1-2000 mg.

4. The method according to claim 2, wherein the therapeutically effective amount administered is in the range of about 1-200 mg per kg of body weight of the subject.

* * * * *